United States Patent [19]
Fukuda et al.

[11] Patent Number: 6,165,740
[45] Date of Patent: Dec. 26, 2000

[54] METHOD AND DEVICE FOR FLOW-CYTOMETRIC MICROORGANISM ANALYSIS

[75] Inventors: Masakazu Fukuda, Kobe; Junya Inoue, Ono; Akito Terai, Kyoto; Kazuyuki Kanai, Kasai; Kurayoshi Iseki, Kakogawa; Mayumi Kamo, Kinosaki-gun, all of Japan

[73] Assignee: Sysmex Corporation, Kobe, Japan

[21] Appl. No.: 09/407,286

[22] Filed: Sep. 29, 1999

[30] Foreign Application Priority Data

Sep. 30, 1998 [JP] Japan ................. 10-276799
Sep. 16, 1999 [JP] Japan ................. 11-262053

[51] Int. Cl.$^7$ ................ C12Q 1/02; C12Q 1/04; C12Q 1/14
[52] U.S. Cl. ................ 435/29; 435/34; 435/36; 435/7.2; 435/7.33; 435/7.34; 435/832; 435/833; 435/834; 435/835; 435/836; 435/837; 435/838; 435/839; 435/882; 435/885; 435/911; 435/283.1
[58] Field of Search ................ 435/29, 34, 36, 435/7.2, 7.33, 7.34, 832, 833, 834, 835, 836, 837, 838, 839, 882, 885, 911, 283.1

[56] References Cited

U.S. PATENT DOCUMENTS 5,701,012 12/1997 Ho ................ 435/29
5,895,922 4/1999 Ho ................ 435/29

Primary Examiner—Louise N. Leary
Attorney, Agent, or Firm—Shinjyu Intellectual Property Firm

[57] ABSTRACT

To reduce the effects of the contaminants in the measurement of microorganisms and the reduction of the time necessary for the measurement. Measurement is performed of the microorganism prior to and following culture, and the difference between the two is found. This prevents errors caused by the effect of contaminants contained in the specimens. Since the measurement of the microorganism is performed by means of a flow cytometer, the microorganisms can be measured even when the culture period is short. Moreover, the measurements are accurate, since the contaminants are not measured. Furthermore, the growth form of the microorganisms can be determined by measuring the changes in the intensity of the light emission over the duration of emission of the forward scattered light detected by means of a flow cytometer. Accordingly, based on differences in the particle-size distribution prior to and following culture, it is possible to formulate five major bacterial classifications: Bacilli, Staphylococci, Streptobacilli, Streptococci and yeast fungi.

8 Claims, 37 Drawing Sheets

Fig. 1
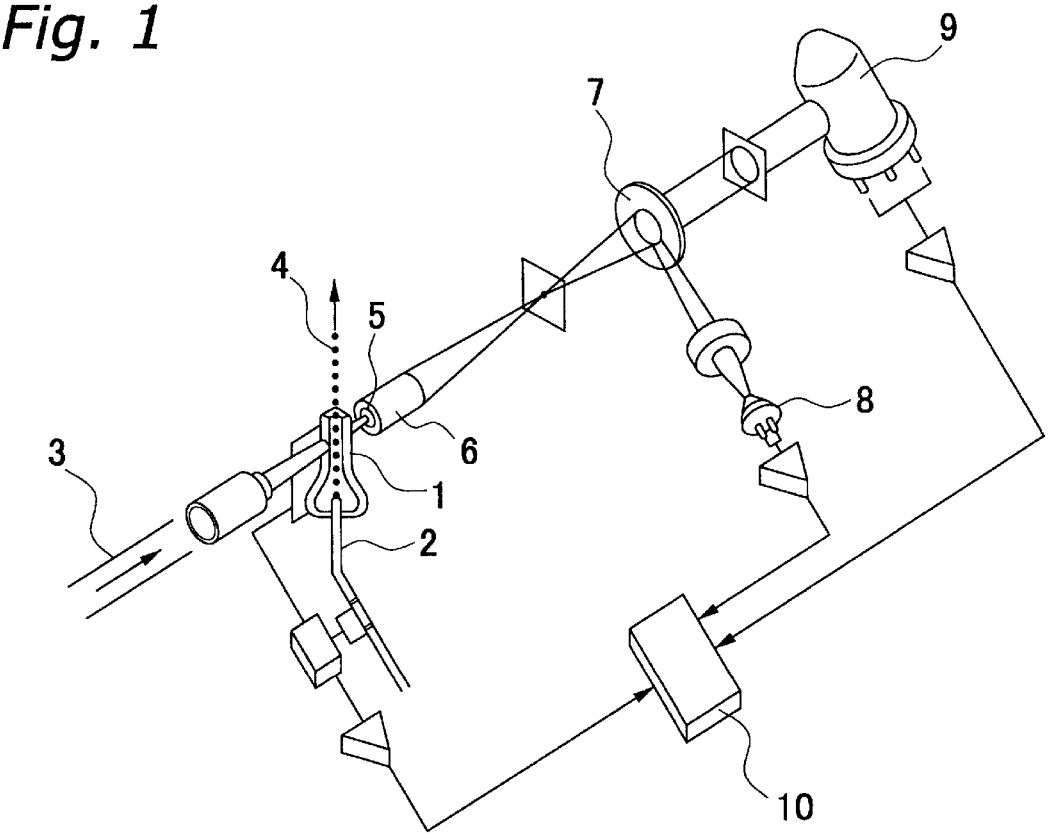
Fig. 2
FORWARD SCATTERED LIGHT SIGNAL
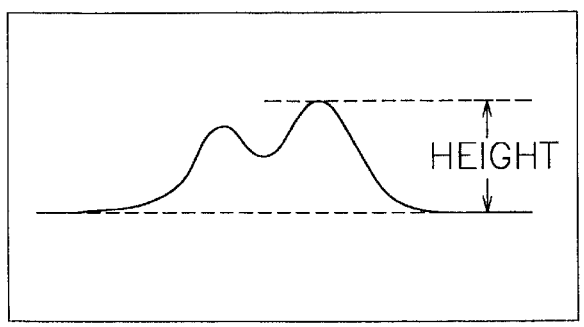
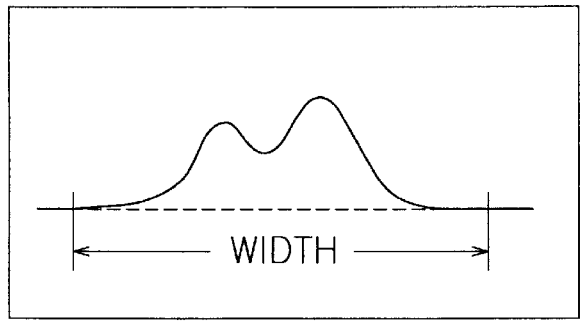

PARTICLE SIZE DISTRIBUTION IN URINE (PRE-CULTURE)

PARTICLE SIZE DISTRIBUTION IN URINE (POST-CULTURE)

PARTICLE SIZE DISTRIBUTION FOR STREPTOCOCCI (POST-CULTURE)

PARTICLE SIZE DISTRIBUTION FOR STREPTOCOCCI (PRE-CULTURE)

PARTICLE SIZE DISTRIBUTION FOR STREPTOBACILLI (POST-CULTURE)

PARTICLE SIZE DISTRIBUTION FOR STREPTOBACILLI (PRE-CULTURE)

PARTICLE SIZE DISTRIBUTION FOR YEAST FUNGI (POST-CULTURE)

PARTICLE SIZE DISTRIBUTION FOR YEAST FUNGI (PRE-CULTURE)

Fig. 15 BACILLI (1) PARTICLE SIZE DISTRIBUTION
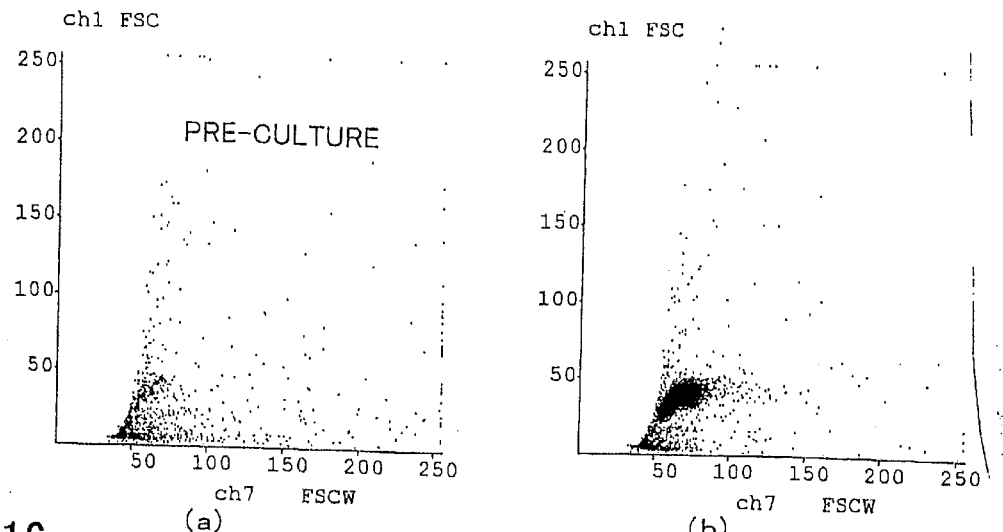
Fig. 16 BACILLI (2) PARTICLE SIZE DISTRIBUTION
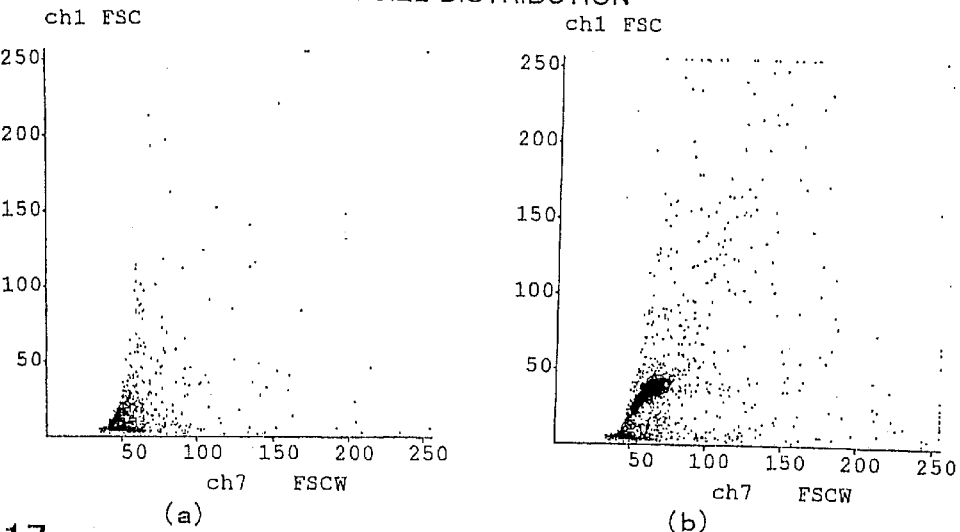
Fig. 17 STAPHYLOCOCCI (1) PARTICLE SIZE DISTRIBUTION
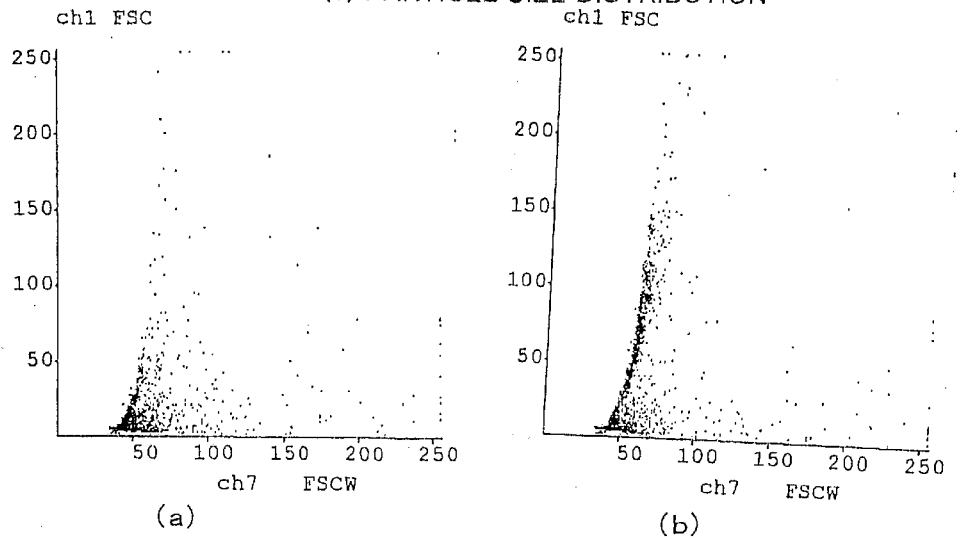

Fig. 18 STAPHYLOCOCCI (2) PARTICLE SIZE DISTRIBUTION
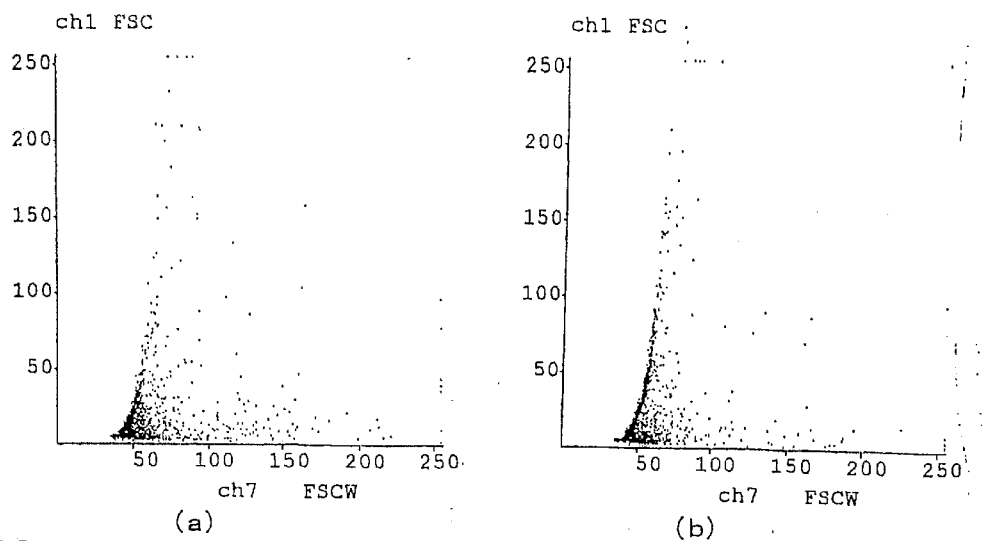
Fig. 19 STREPTOCOCCI (1) PARTICLE SIZE DISTRIBUTION (1)
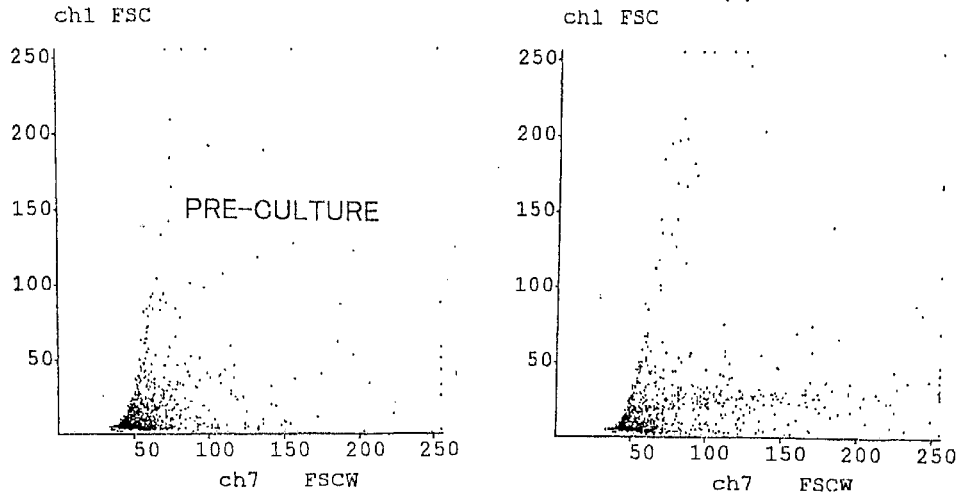
Fig. 20 STREPTOCOCCI (2) PARTICLE SIZE DISTRIBUTION
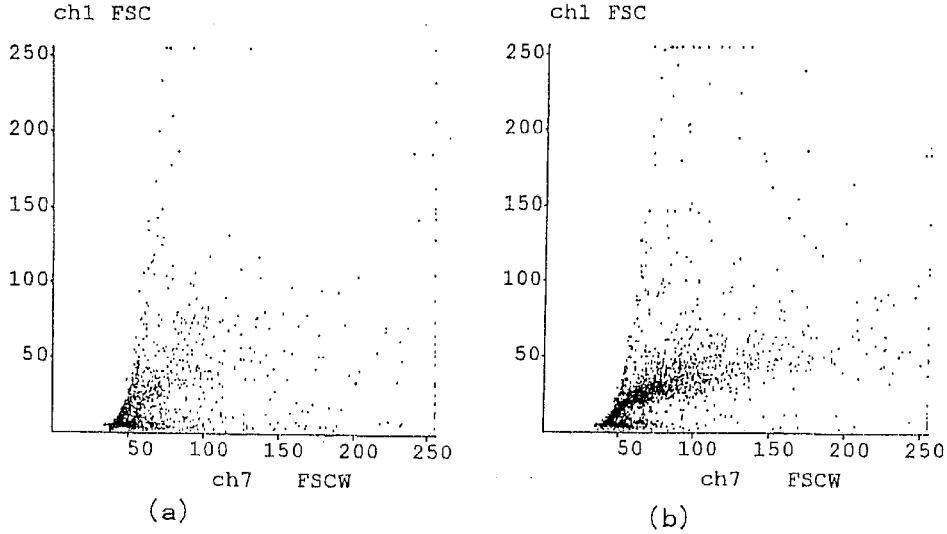

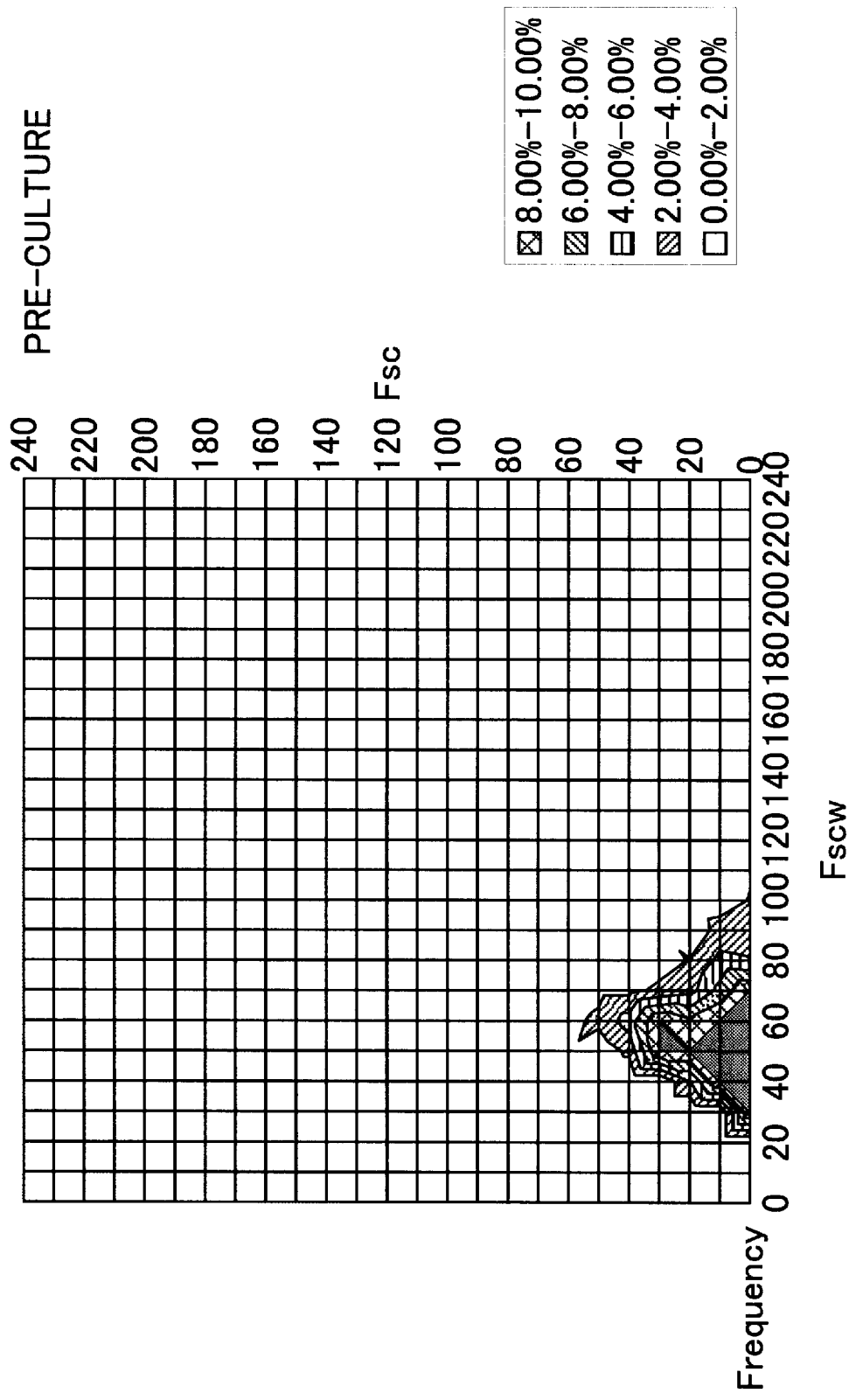
Fig. 21a  ASSAY RESULTS FOR BACILLI (1)  PRE-CULTURE

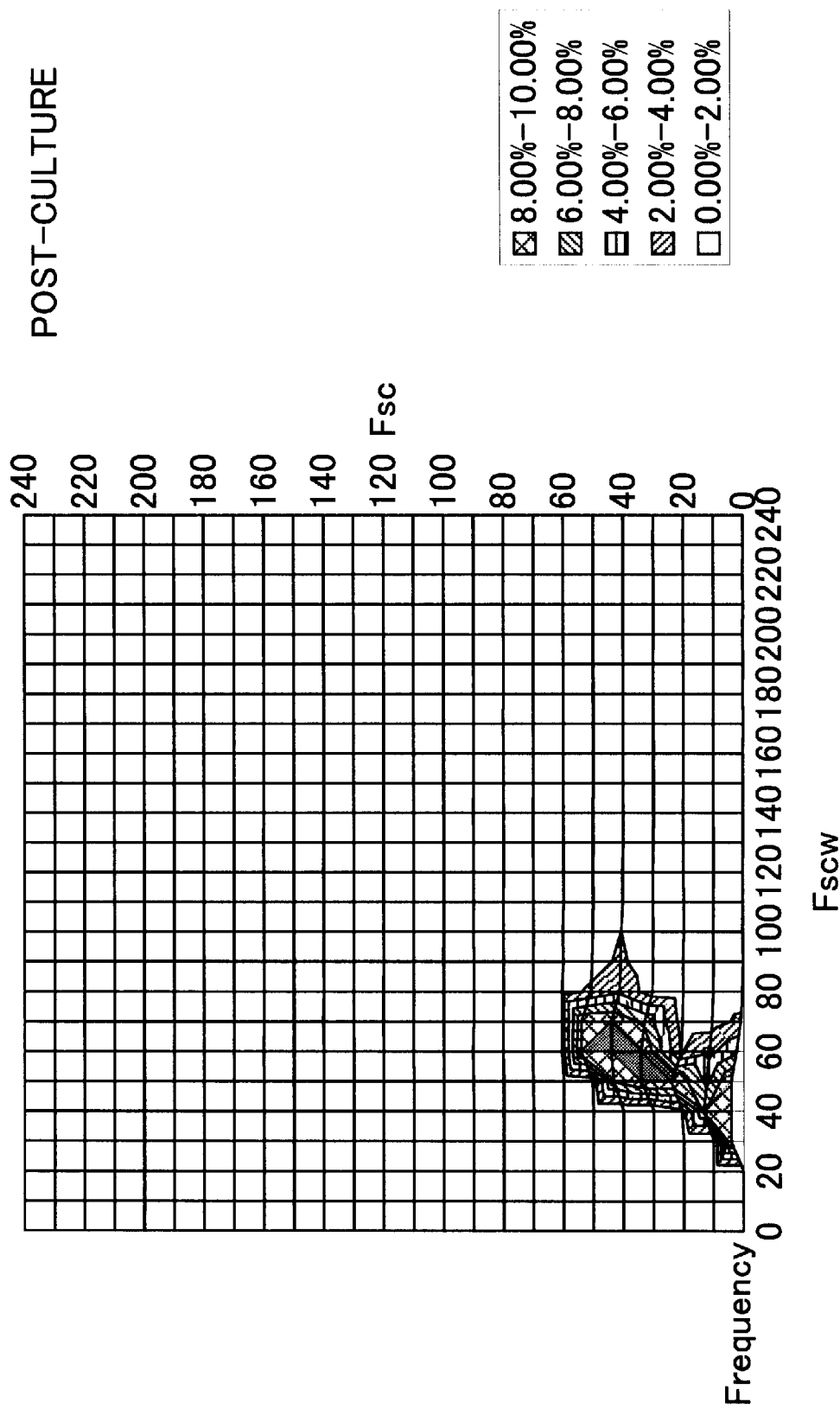

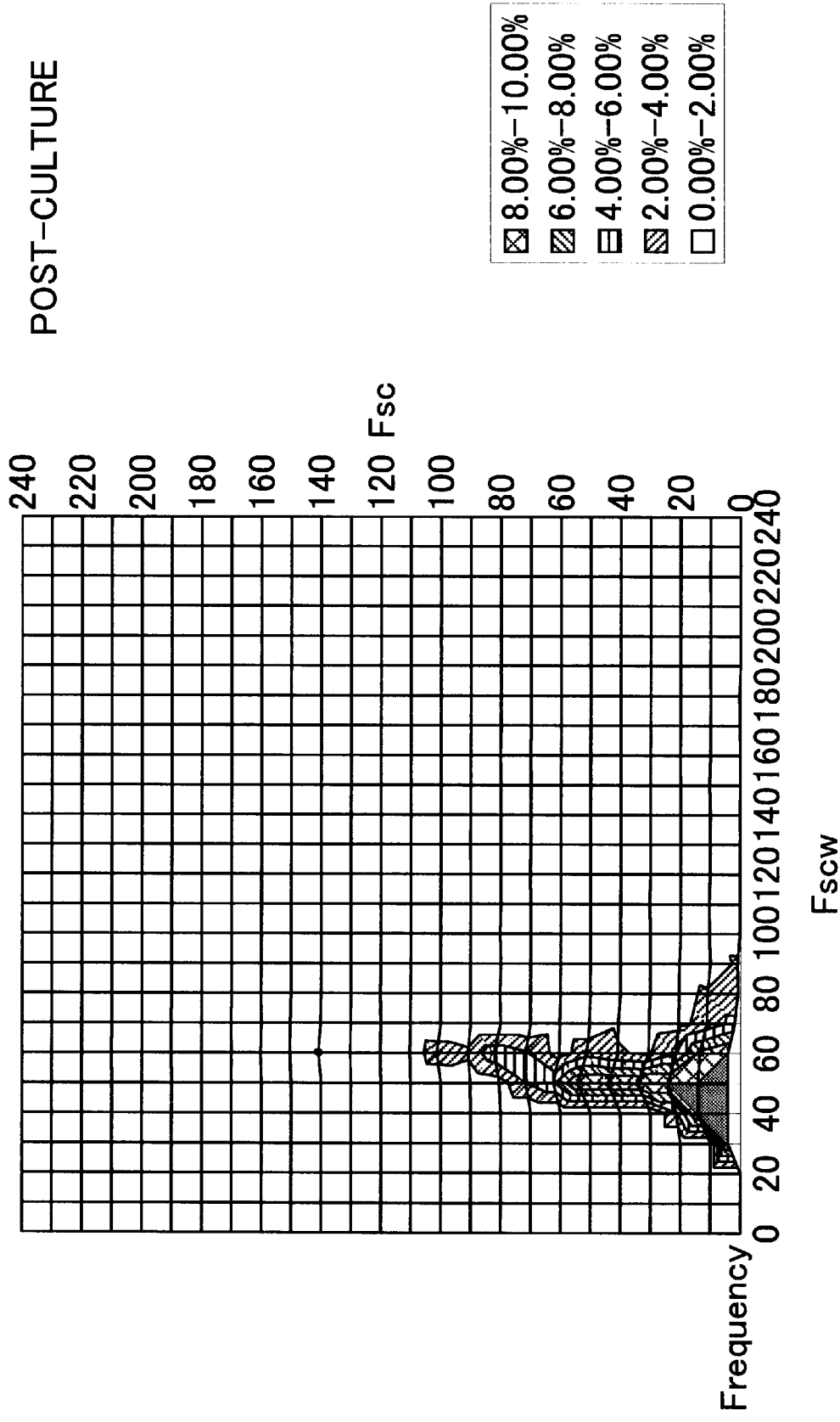
Fig. 24b ASSAY RESULTS FOR STAPHYLOCOCCI (2) POST-CULTURE

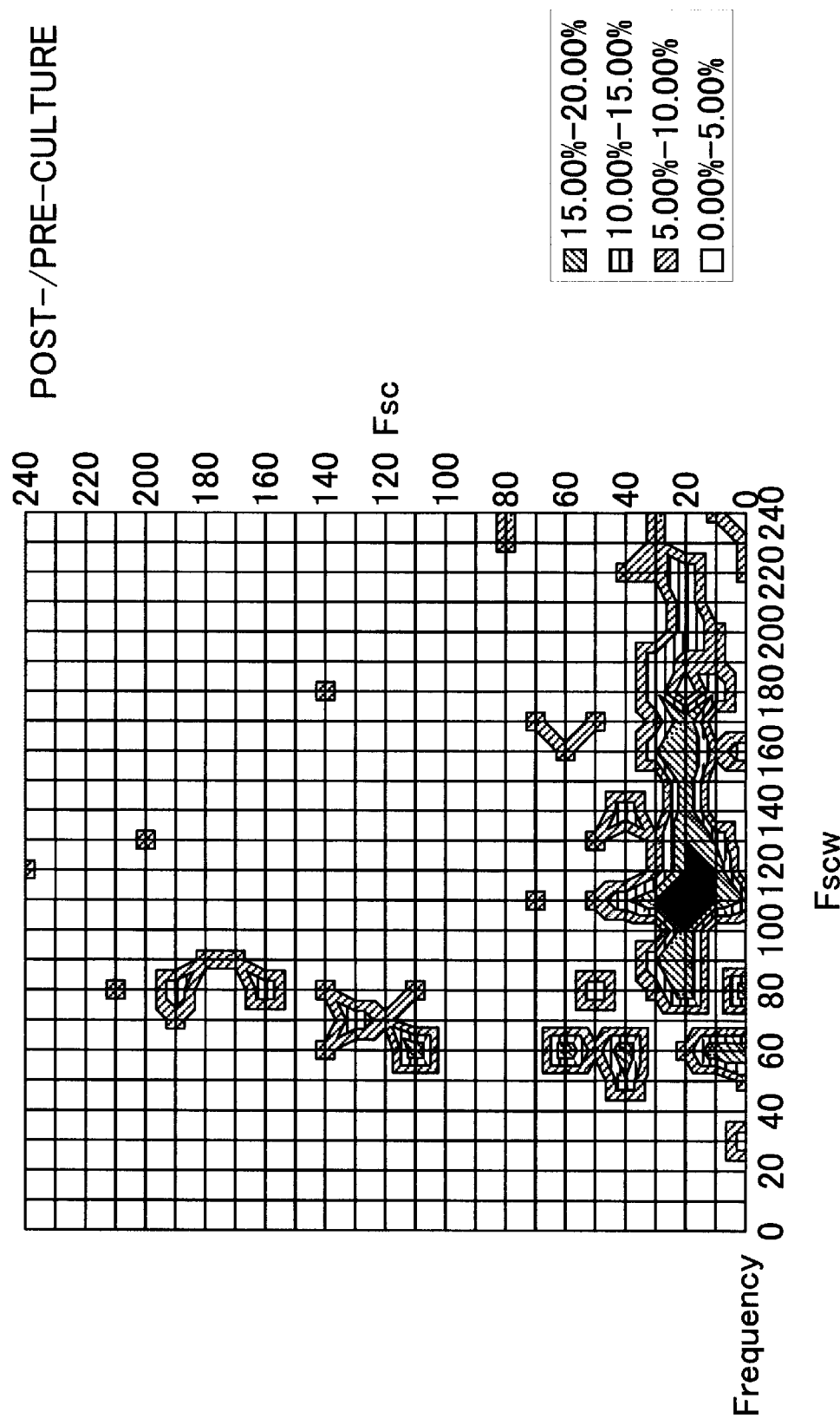

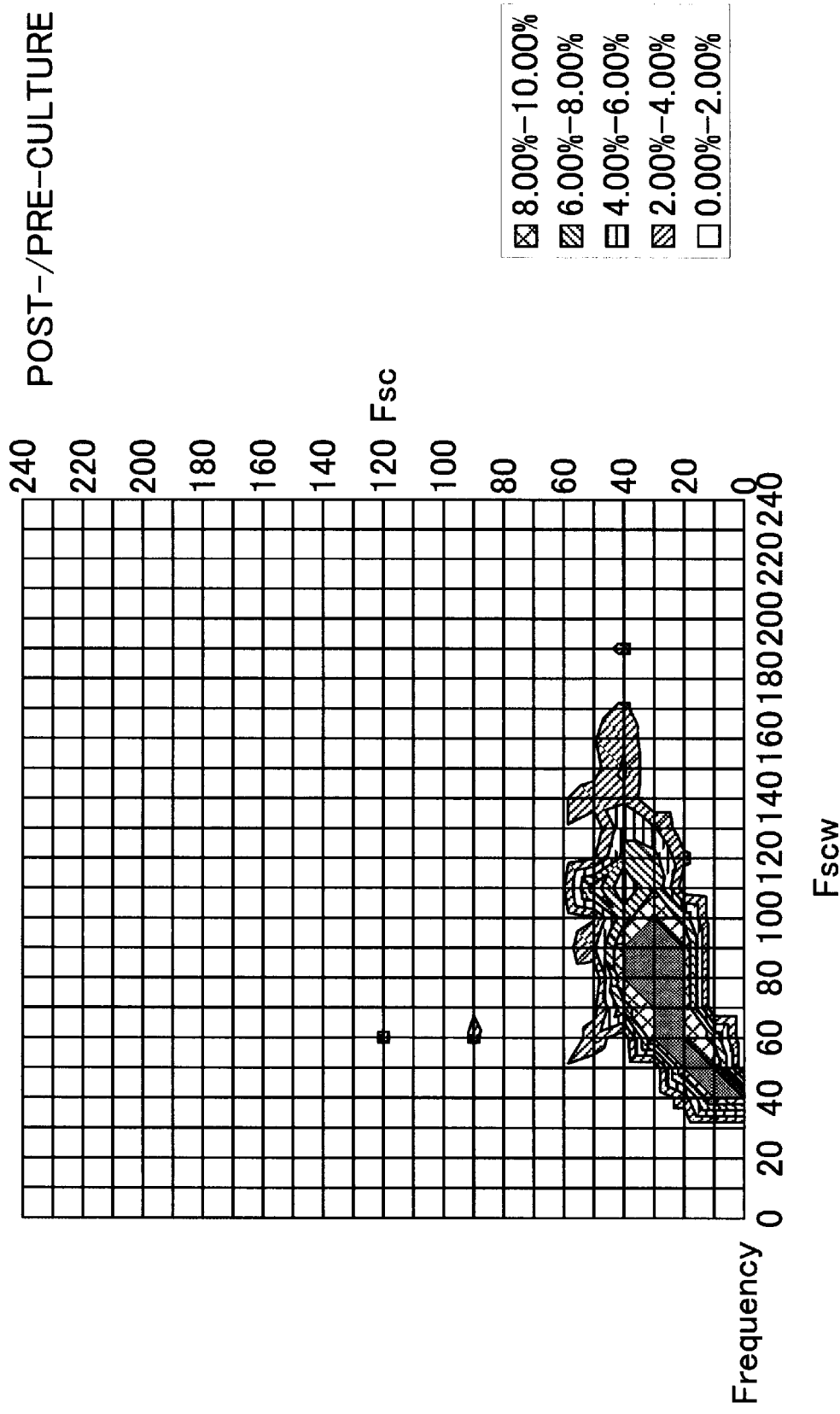

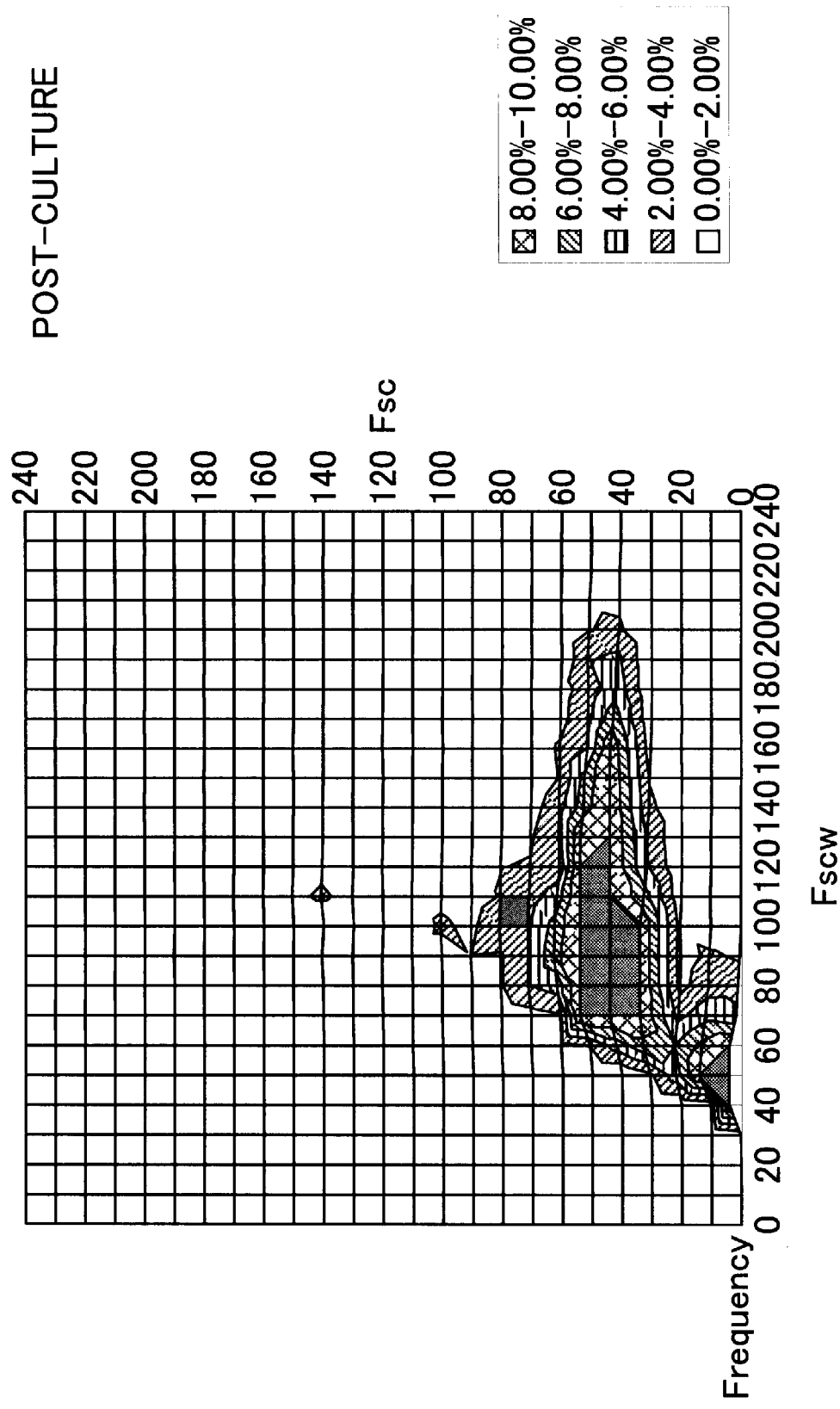
Fig. 27b ASSAY RESULTS FOR STREPTOBACILLI (1) POST-CULTURE

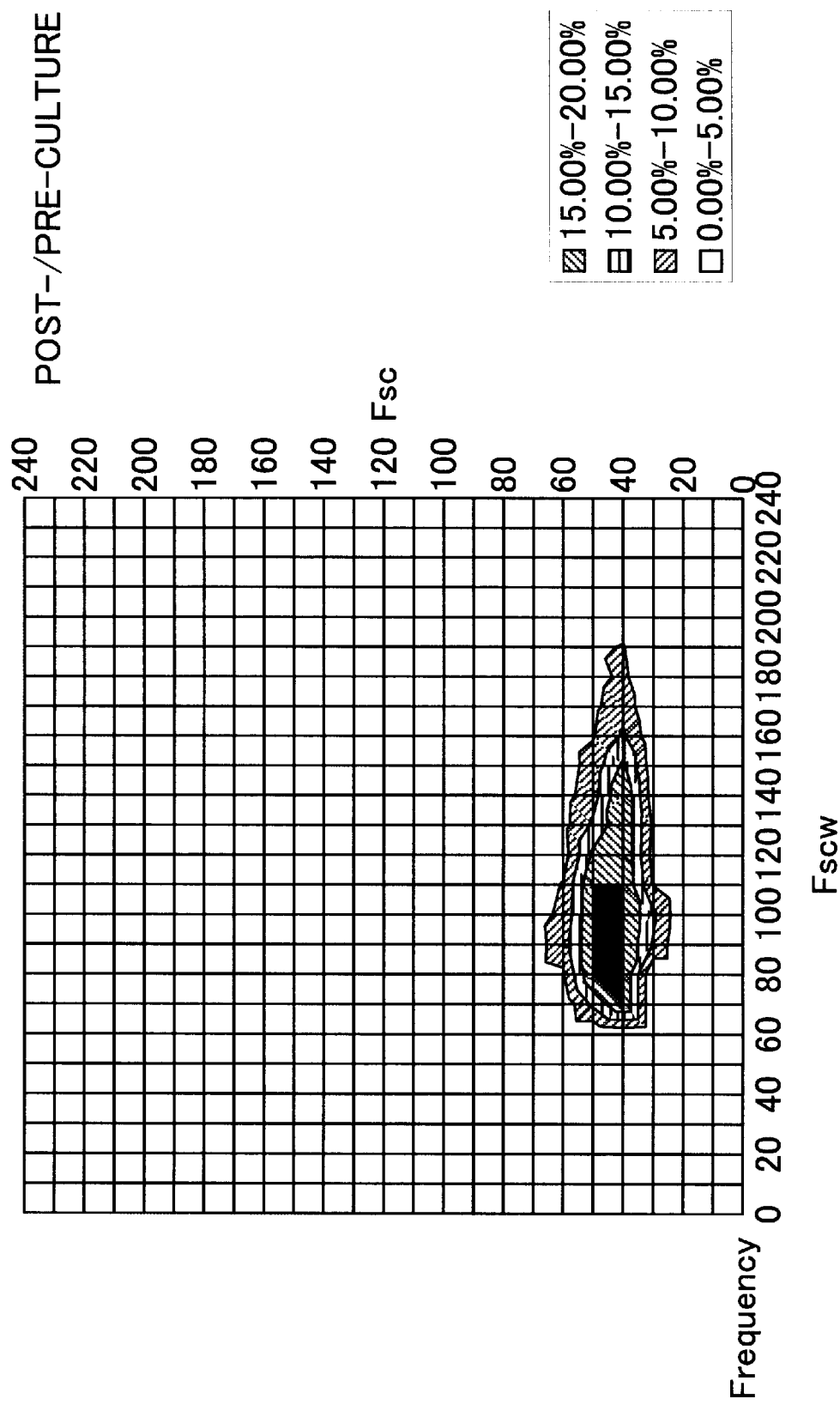

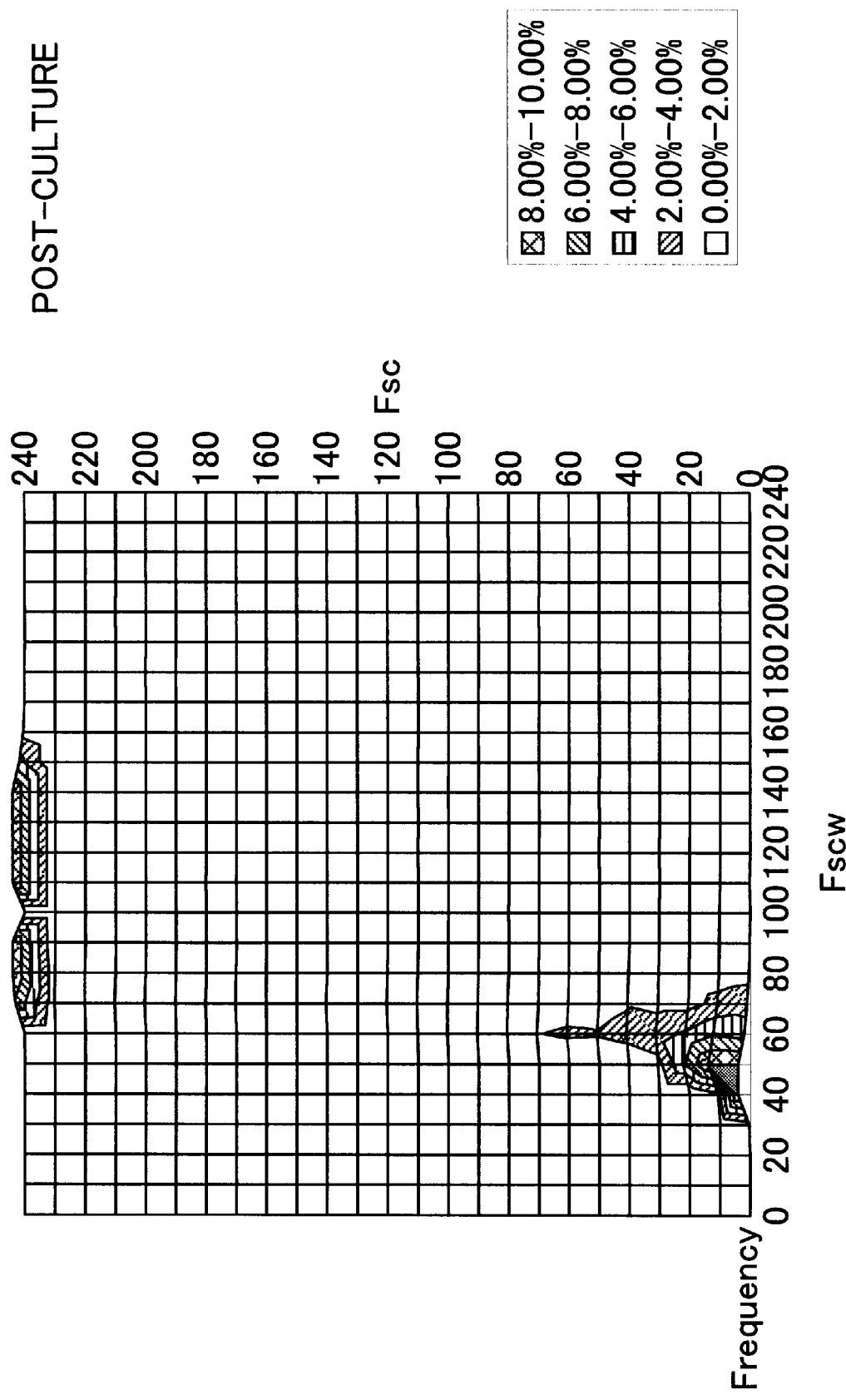

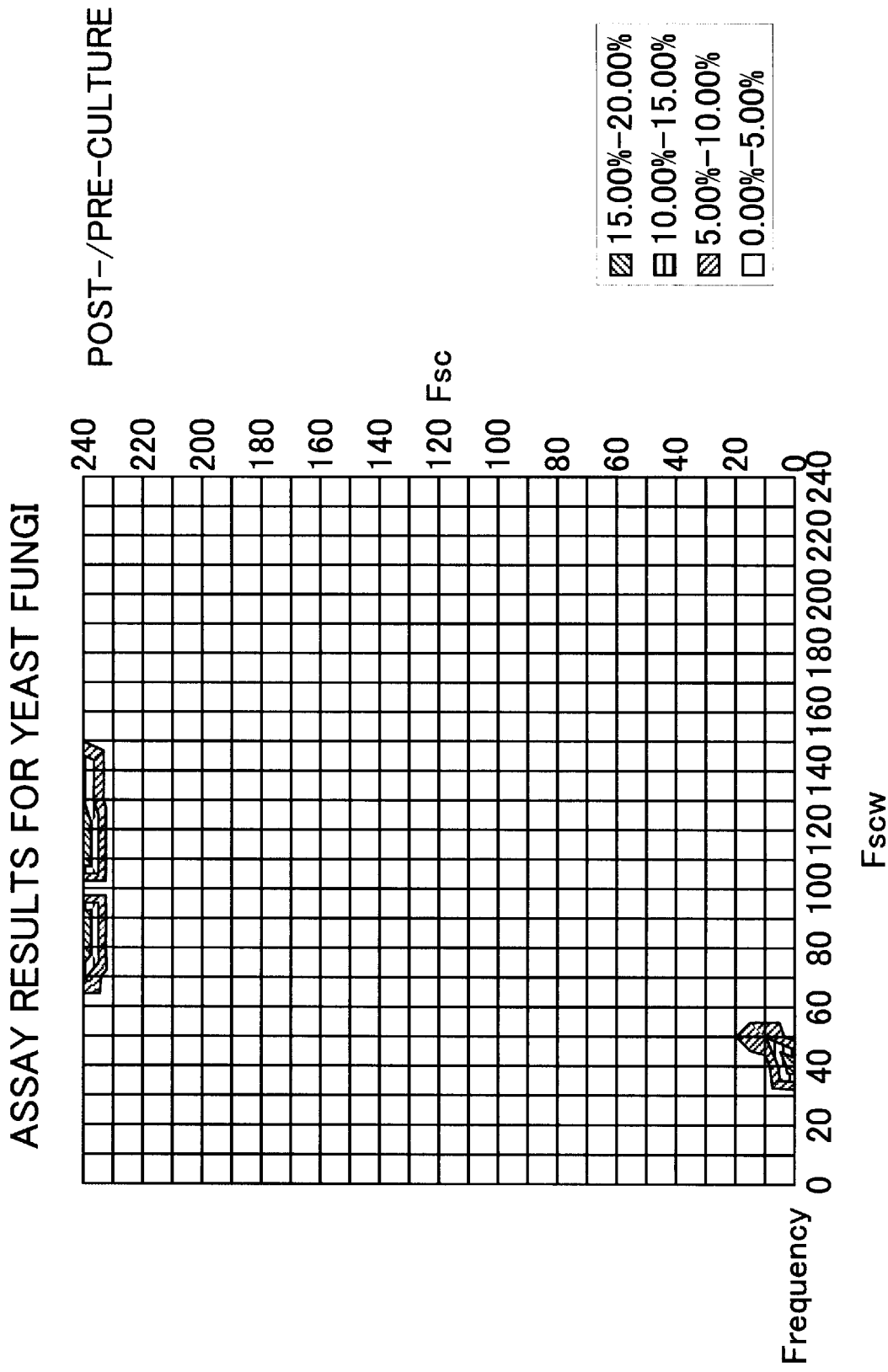

METHOD AND DEVICE FOR FLOW-CYTOMETRIC MICROORGANISM ANALYSIS

BACKGROUND OF THE INVENTION

1. Technical Field

The present invention relates to methods for culturing bacteria and other culturable microorganisms to measure the germ counts. More specifically, it relates to a microorganism analyzing method in which the germ count can be measured quickly and in a highly sensitive manner, even in samples that include contaminants other than microorganisms.

2. Description of Related Art

The conventional method that has generally been used to culture microorganisms and to measure their number is the agar plate smear method. In this method, a prescribed amount of a specimen is smeared onto an agar plate culture, which contains appropriate nutrients. The specimen is cultured until the colony is large enough to be observed macroscopically, and then the resulting colony is measured. When this method is used, however, one must wait until the bacterial colony grows to a size that is large enough to be observed macroscopically. Therefore, a culture period of 18 to 24 hours is generally the extent required for inferring what the category of bacteria is. Depending on the type of bacteria, there are some that require a culture period in excess of 24 hours, in excess of 48 hours, and even those that require a long-term period extending one month.

Depending on the type of bacteria that are grown in the culture, there are occasions that require germ-type identification screening to single out microorganisms, or that require drug sensitivity tests to examine the efficacy of certain drugs. With the conventional method, however, judging the need for these tests takes time; moreover, efficiently screening a large number of samples is difficult.

Instead of agar plate culture, samples can be cultured by a method employing liquid culture. According to this method, a fixed volume of the specimen is combined with a liquid culture that contains the appropriate nutrients; culture is thus performed, and the turbidity is measured macroscopically, or by means of an absorption photometer or a spectrophotometer. Photometers are not known to have fine sensitivity; thus, when this method is used, one must wait for the growth of the bacteria, until there is a change in the turbidity. For this reason, the measurement of the number of bacteria, as in the case of the agar smear plate method, requires several days of culture. This results in the aforementioned problems.

Moreover, Japanese Laid-open Patent Application No. 5-82901 discloses a method for counting bacteria by irradiating the specimen in the culture with light and by observing the changes over time of the scattered light and the transmitted light. By using this method, one can find accurate germ counts, even wherein the germs differ in developmental form. Since this method utilizes the changes in the scattered light data and the changes in the transmitted light data as the bacteria grows, the time needed for the specimen culture cannot be shortened.

Meanwhile, particle measurement devices, flow cytometers in particular, are known to be highly sensitive devices for measuring extremely small particles, such as microorganisms. Since particle measurement devices calculate each and every particle in a sample, it is possible to perform highly sensitive measurements. Accordingly, by using a particle measurement device, it is possible to measure the number of bacteria in the sample, without long hours for culturing.

Particle measurement devices, however, detect all particles that are the size of microorganisms, including contaminants such as dust and precipitants, as microorganisms. Thus, detection results of particle measurement devices invariably contain errors caused by the measurement of contaminants. When urine, for example, is used as a specimen and is measured for bacteria, the components in the urine that have such physical forms, as erythrocytes, leukocytes, epitheliocytes, casts, crystals and fragments thereof, are detected as bacteria.

Therein, to differentiate between contaminants and microorganisms, a method of staining microorganisms with fluorescent dyes and measuring the fluorescence they emit has been advocated. The degree of staining, however, differs according to the type of microorganism. Moreover, fluorescent dyes and treatment conditions for staining only the targeted microorganisms must be established according to each sample. Thus, a great deal of trouble is required to perform the analysis; this staining method is not suited to assaying large quantities of specimens.

Other methods for the rapid detection of microorganism counts include: measuring changes in the impedance of the culture that accompanies the growth of the microorganisms, measuring changes in the pH of the culture fluid, and measuring amounts of consumed oxygen or carbon dioxide produced, and research has recently been conducted on methods of finding microorganism counts from correlations between these measurements and microorganism counts. It is possible, however, that these measurement values will change due to causes apart form the microorganisms cultured. Moreover, when considering limitations in the microorganisms that can be detected and the degree of accuracy, these methods cannot be considered satisfactory. These methods can only be used under special conditions. In other words, as has been shown above, there is no method as yet that is capable of conducting the measurement of microorganisms in specimens both accurately and in a brief period of time.

SUMMARY OF THE INVENTION

Taking such circumstances into account, the object of the present invention is to enable a method for measuring microorganisms in a culture easily, accurately and in a short interval.

The invention in this application, to address the problems described above, in a first aspect is a method of analyzing microorganisms in a culture sample wherein the specimen to be measured has been added to a liquid culture, the microorganism analyzing method characterized in including:

(A) a first measurement process for obtaining a first particle-size distribution in the culture sample from scattered-light optical information detected employing a flow cytometer to measure the culture sample after culturing the sample for a predetermined time period;

(B) a second measurement process for obtaining a second particle-size distribution in the culture sample from scattered-light optical information detected employing the flow cytometer to measure the culture sample before culturing the sample;

(C) an assay process for obtaining a particle-size distribution of microorganisms cultured in the culture sample, from the difference between the first particle-size distribution and the second particle-size distribution; and (D) an output process for outputting the obtained microorganism particle-size distribution.

By subtracting the measurement results before culture from the measurement results after culture, it is possible to measure the microorganisms excluding contaminants. Contaminants refer, for example, to dust and formed elements of the specimens.

The present invention in a second aspect is the microorganism analyzing method of the invention in its first aspect, but further wherein the emission duration and intensity of the scattered light signals detected using the flow cytometer are measured to obtain the first and second particle-size distributions.

The intensity of the scattered light provides information concerning the size of the particles contained in the culture sample. The timing of the scattered light emission provides information concerning the length of the particle bodies contained in the culture sample. Therefore, by measuring the emission duration and intensity of the scattered light, it is possible to distinguish the growth form, such as growth in concatenated (streptococcal) formation or in grape-cluster formation.

The present invention in a third aspect is the microorganism analyzing method of the invention in its first aspect, but further wherein the emission duration and intensity of the scattered light signals detected using the flow cytometer are measured to obtain the particle-size distribution of the cultured microorganisms, to infer the growth form of the microorganisms based on the particle-size distribution, and to determine to which predetermined category the microorganisms belong.

It can be inferred that when the diameter of the growing bacteria is relatively large and the length is not extremely long, the microorganisms are Staphylococcus bacteria (staphylococci); that when the diameter of the growing bacteria is relatively small and the length is short, the microorganisms are Bacillus bacteria (bacilli); that when the diameter of the growing bacteria is relatively small and the length is long, the microorganisms are Streptobacillus bacteria (streptobacilli); and that when the diameter is even smaller and the length is longer than those of the streptobacilli, the microorganisms are Streptococcus bacteria (streptococci).

The present invention in a fourth aspect is the microorganism analyzing method of the invention in its first aspect, but further wherein the emission duration and intensity of the scattered light signals detected by using the flow cytometer are measured to obtain the particle-size distribution of the cultured microorganisms, and the category to which each of the growth forms of the microorganisms belongs is determined based on the particle-size distribution, similarly as in the third aspect of the invention, but specifically from among the staphylococi, streptococci, streptobacilli and bacilli.

The present invention in a fifth aspect is the microorganism analyzing method of the invention in its first aspect, but further wherein the specimen to be measured is urine.

When urine is used as a specimen, it is possible to distinguish Gram negative/positive bacteria from the classification results for the microorganisms.

The present invention in a sixth aspect is the microorganism analyzing method of the invention in its first aspect, but further wherein the microorganisms that are measured are bacteria and/or yeast fungi.

The present invention in a seventh aspect is a microorganism analyzer, used along with a flow cytometer, for analyzing particle size of microorganisms in a culture sample wherein the specimen to be measured has been added to a liquid culture. The microorganism analyzer comprises a first measurement means, a second measurement means, an assay means and an output means. The first measurement means obtains a first particle-size distribution of the culture sample, after culture for a prescribed length of time, from the optical information of the scattered light detected by the flow cytometer. The second measurement means obtains a second particle-size distribution of the culture sample, before culture, from the optical information of the scattered light detected by the flow cytometer. From the difference between the first particle-size distribution and the second particle-size distribution, the analytical means obtains the particle-size distribution of the microorganisms cultured in the culture sample. The output means outputs the particle-size distribution of the microorganisms thus obtained.

The method in accordance with the invention in its first aspect may be executed in the microorganism analyzer of the seventh aspect of the invention.

The present invention in an eighth aspect is a computer-readable recording medium containing an assaying program utilized together with a flow cytometer. The flow cytometer measures particle size of microorganisms in a culture sample wherein the specimen to be measured has been added to a liquid culture. The assaying program contained on the computer-readable recording medium is for assaying the results of the particle size measurements made by the flow cytometer, and is for executing steps A through D below.

(A) a step of obtaining a first particle-size distribution in the culture sample after it has been cultured a predetermined time period, from scattered-light optical information detected by the flow cytometer;

(B) a step of obtaining a second particle-size distribution in the culture sample before it has been cultured, from scattered-light optical information detected by the flow cytometer;

(C) a step of obtaining a particle-size distribution of microorganisms cultured in the culture sample, from the difference between the first particle-size distribution and the second particle-size distribution; and (D) a step for outputting the obtained microorganism particle-size distribution.

Employing the present invention easily and rapidly measures the microorganisms in a culture utilizing a flow cytometer, and reduces the effect that contaminants produce on the measurement results, providing accurate measurements.

Furthermore, from the duration of the scattered light emission and from the signal intensity which are detected by flow cytometer, a breakdown classifying the microorganisms can be inferred, curtailing the time needed for the tests.

The foregoing and other objects, features, aspects and advantages of the present invention will become more apparent from the following detailed description in conjunction with the accompanying drawings.

BRIEF DESCRIPTION OF THE DRAWINGS

FIG. 1 is an explanatory diagram depicting the structure of a detector section in a flow cytometer;

FIG. 2 is an explanatory diagram depicting signal input into the flow cytometer;

FIG. 15(a) graphs pre-culture particle-size distribution of Bacilli (1), and (b) graphs post-culture particle-size distribution of the Bacilli (1);

FIG. 16(a) graphs pre-culture particle-size distribution of Bacilli (2), and (b) graphs post-culture the Bacilli (2);

FIG. 17(a) graphs pre-culture Staphylococci (1), and (b) graphs post-culture particle-size distribution of the Staphylococci (1);

FIG. 18(a) graphs pre-culture particle-size distribution of Staphylococci (2), and (b) graphs post-culture particle-size distribution of the Staphylococci (2);

FIG. 19(a) graphs pre-culture particle-size distribution of Streptococci (1), and (b) graphs post-culture particle-size distribution of the Streptococci (1);

FIG. 20(a) graphs pre-culture particle-size distribution of Streptococci (2), and (b) graphs post-culture particle-size distribution of the Streptococci (2);

DETAILED DESCRIPTION OF THE PREFERRED EMBODIMENTS

Figure 3:
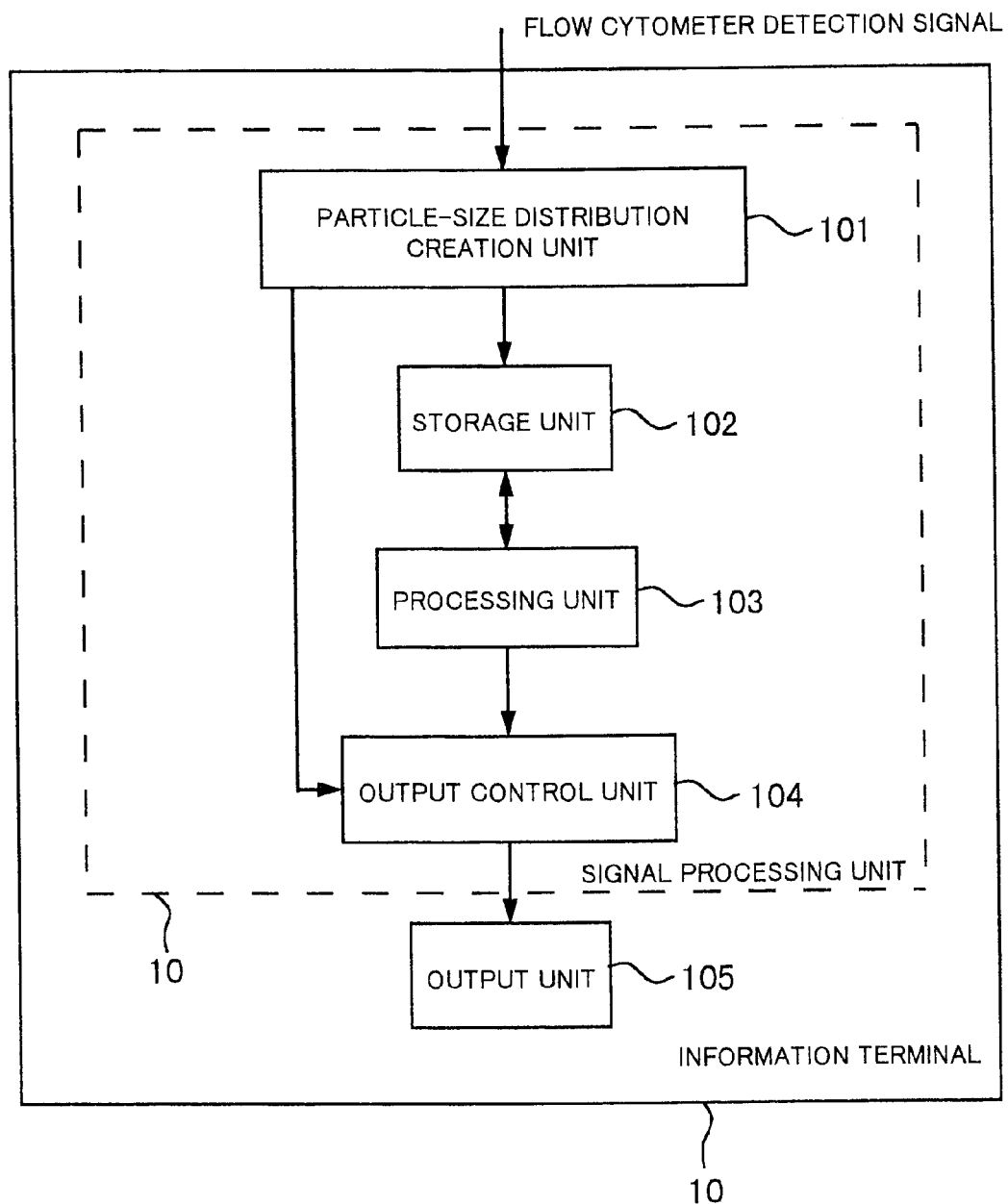
FIG. 3 is a block figure showing the working structure of a signal-processing unit in accordance with the invention.

The present invention will be explained in detail while presenting embodiments.

In the present invention, the flow cytometer is a device wherein a) a sample is enveloped in a sheath solution and flowed, which by hydrodynamic effects forms a narrow sample stream; b) the particles in the sample are flowed, one by one, to the detector unit; and c) the sample stream is irradiated with light, and scattered light and fluorescent light emitted from the particles is detected. A semiconductor laser or an argon laser may be suitably utilized as the light source.

The culture solution is a liquid culture medium that includes the appropriate nutrients for the culture of microorganisms. The culture medium can be selectively used. A general bacterial medium can be used when a microorganism type is not specified, and an appropriate bacterial medium can be used when a microorganism type is specified.

Culturing microorganisms is a process in which a culture sample is placed in an incubator at a prescribed temperature (at 30 to 37° C., for example), to promote microorganism cultivation.

Measuring culture samples before culturing also includes the process of conducting the measurement after the culture sample is kept at a temperature low enough to prevent the growth of microorganisms.

FIRST EMBODIMENT

The present invention will be explained on the basis of the embodiments illustrated in the figures. It will be understood, however, that the present invention is not limited to these examples.

Devices:

FIG. 1 depicts a structural representation of the present invention, including a detector unit of the flow cytometer and a signal-processing unit 10.

The detector unit of the flow cytometer has a sheath flow cell 1; a sample nozzle 2; a beam stopper 5; a collector lens 6; a dichroic filter 7; a photo diode 8; and a photomultiplier 9.

The sheath flow cell 1 envelops the sample that flows from the sample nozzle 2 with a sheath liquid, thereby forming a flow sample 4 enveloped in the sheath solution. The flow sample particles 4 are irradiated by laser beam pulses 3 from a laser source that is not indicated in the figure. The beam stopper 5 stops light that is transmitted directly through the flow sample 4. The collector lens 6 condenses forward scattered light and forward fluorescent light discharged by the particle 4. The dichroic filter 7 reflects the forward scattered light. The photo diode 8 detects the forward scattered light reflected by the dichroic filter 7. The detected forward scattered light is input into a signal-processing unit 10 via an amplifier. The photomultiplier 9 detects the forward fluorescent light that has passed through the dichroic filter 7. The forward scattered light and the forward fluorescent light detected by the photo diode 8 and the photomultiplier 9 are input respectively into the signal-processing unit 10 via an amplifier.

The signal-processing unit 10 in the present invention receives the detector signal output from the photo diode 8, based upon which it measures forward scattered light intensity (Fsc) and forward scattered light width (Fscw) of the pulses. The signal-processing unit 10 also creates and analyzes a particle-size distribution graph, based upon the forward scattered light signal. FIG. 2 shows a conceptual figure of the signal input into the signal-processing unit 10. The intensity of the scattered light corresponds to the intensity of the input signal, which, in other words, corresponds to the height of the pulse. The emission time of the scattered light corresponds to the pulse width of the input signal.

FIG. 3 is a block figure that shows the functional structure of the signal-processing unit 10. The signal-processing unit 10 is provided on an information terminal such as a personal computer or work station, and comprises a particle-size distribution creation unit 101, a memory 102, a processing unit 103 and an output control unit 104.

Figure 6:
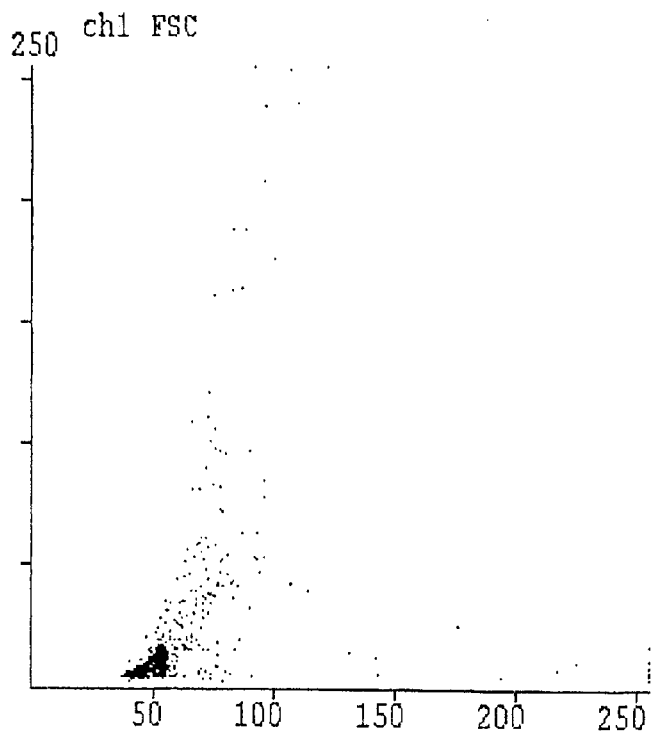
FIG. 6 is a particle-size distribution graph following culture from a urine sample.

The particle-size distribution creation unit 101 receives the light signal detected by the flow cytometer, and, based on the received signals, creates a particle-size distribution wherein the horizontal axis is the duration of the emission of the forward scattered light and the vertical axis is the intensity of the emission of the forward scattered light. The particle-size distribution creation unit 101 can output the created particle-size distribution graph showing the particle-size distribution to a display or other output unit via the output control unit 104. FIG. 6, 7, and subsequent figures, which will be discussed below, are examples of particle-size distribution graphs output by the particle-size distribution creation unit 101.

The memory 102 stores the created particle-size distribution, both prior to and following culture. The memory 102 also stores the results of analyzing the block section data, created based on the particle-size distribution graph, as well as the particle-size distribution graph itself. The block section data and its analysis results will be discussed below.

The processing unit 103 subdivides the particle-size distribution graph into predetermined block sections and seeks the data number in each block section (hereafter referred to simply as "block section data"). In other words, the block section data represent the number of particles that are contained in a single block section of a particle-size distribution graph. Moreover, the processing unit 103 seeks changes in the block section data within the same block section, in the particle-size distribution both prior to and following the culture. As a result, it is possible to reduce the errors in the measurements caused by measuring the contaminants in the sample as microorganisms.

An explanation will be presented on measurement errors caused by contaminants. The flow cytometer detection function using the intensity of the forward scattered light will also detect contaminants 1 $\mu$m and smaller, approximately the same size as the microorganisms within the culture solution. A large number of particles will be detected even before culture. (See FIG. 6 below.) Even if particles are detected in large numbers following culture, it is impossible to determine whether they are microorganisms that grew there or whether they are contaminants that were originally present. Thus, the particle-size distribution prior to culture is subtracted from the particle-size distribution following culture, so that only the particles that grew as a result of the culture, that is, only the microorganisms that were cultured, are detected.

The processing unit 103 uses a predetermined method to analyze the particle-size distribution, based on block section data and changes therein, and the analysis results are output to the display control unit. For example, if the block section with the most change is set at 100%, the proportion of change in each block section data is sought, and block sections below a set proportion can be displayed. In order to visually display the degree of change of the block section data, the processing unit 103 selects colors for each block section, corresponding to the degree of change. In the particle-size distributions prior to and following culture, the processing unit 103 may similarly select colors corresponding to the size of the block section data.

Figure 21C:
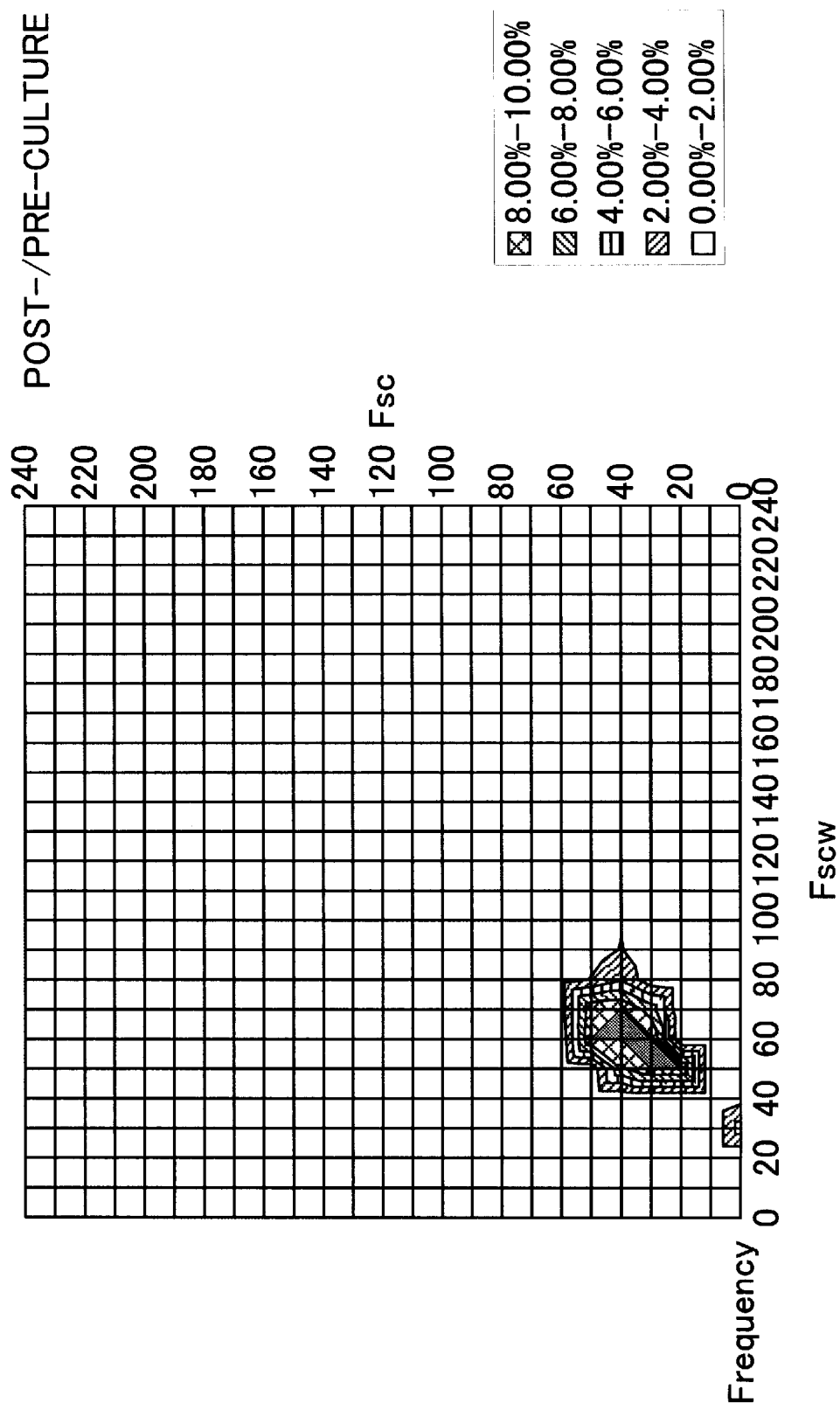
FIG. 21 graphs particle-size distribution assay results for Bacilli (1)

The output control unit 104 uses the display colors selected by the processing unit 103, and outputs the block sections to an output unit, such as a display or printer. FIG. 21 to 28, which will be explained later, represent display examples of the analysis results output by the output control unit 104. The vertical axes represent the scattered light intensity (Fsc), and the horizontal axes represent the scattered light emission time, or pulse width (Fscw). For example, FIG. 21 shows, for Bacilli, respective analytical results of particle-size distribution prior to culture, particle-size distribution following culture, and particle-size distribution of the increase in microorganisms due to the culture.

Process Flow

Figure 4:
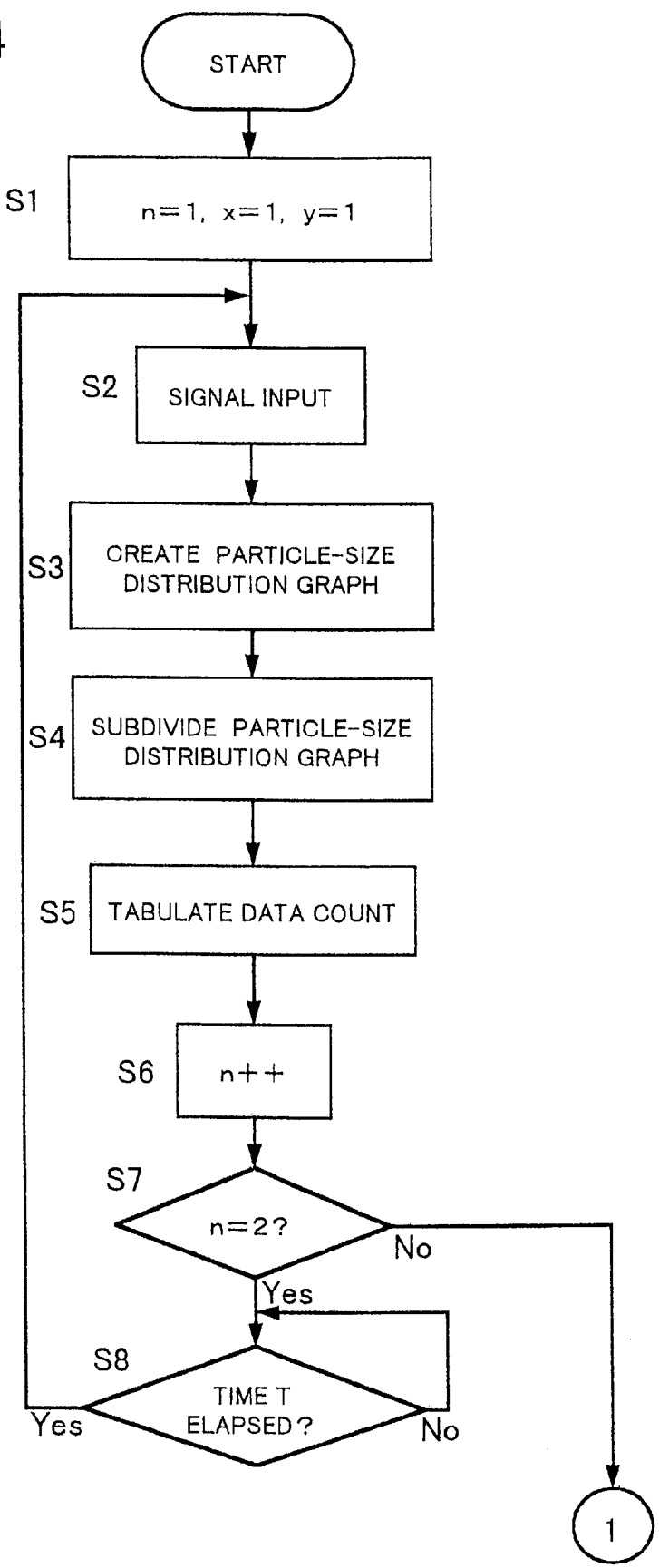
FIG. 4 is a flow chart illustrating the earlier half of analytical process flow executed by the signal-processing unit.
Figure 5:
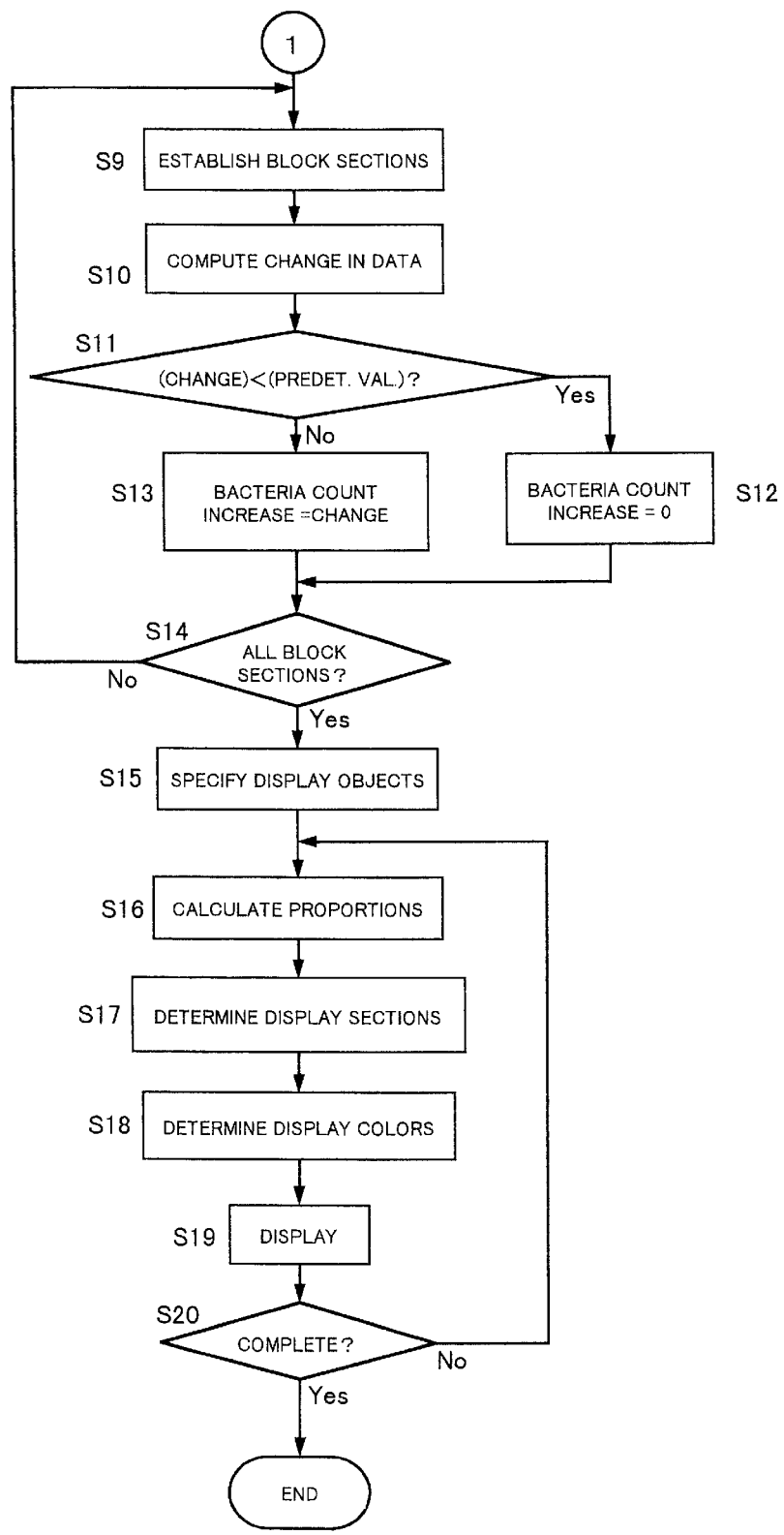
FIG. 5 is a flow chart illustrating the later half flow of the analytical process flow executed by the signal-processing unit.

An explanation will now be given of the processing flow of the analysis performed by the signal-processing unit 10. FIG. 4 shows a flow chart indicating an example of the processing flow of the analysis that is performed by the signal-processing unit 10. The following routine commences when the detection signal is input from the flow cytometer.

First, in step Si, the processing unit 103 performs a predetermined initialization process. Specifically, the processing unit 103 makes the following settings: n=1, x=1 and y=1. Here, n is a variable that indicates the number of measurements, and x and y represent variables that signify positions in the x-axis direction and the y-axis direction in the block sections of the subdivided particle-size distribution graph.

In step S2, the particle-size distribution creation unit 101 receives the detection signal from the flow cytometer.

In step S3, the particle-size distribution creation unit 101 seeks the intensity of the light emission over the duration of the forward scattered light emission based on the received detection signal. The particle-size distribution creation unit 101 stores the created particle-size distribution in the memory 102. The particle-size distribution creation unit 101 reads the particle-size distribution from the memory 102, either in response to a command from the user or automatically, which can be output to a display or the like.

In step S4, the processing unit 103 subdivides the particle-size distribution graph into a predetermined number of block sections. For example, the graph may be subdivided into 256×256 block sections ($1 \leq x \leq 256$, $1 \leq y \leq 256$).

In step S5, the processing unit 103 seeks the block section data for each of the block sections and retains the data in the storage unit. In other words, the processing unit 103, based on the particle-size distribution, seeks the number of particles contained in each of the block sections in the particle-size distribution graph.

In step S6, the processing unit 103 presents the measurement number n in increments.

In step S7, the processing unit 103 determines whether or not the measurement number n is 2. If "yes," step S8 follows, wherein the measurement is executed a second time. If "no," process flow proceeds to step S9, which will be explained below. The measurement of the particle-size distribution prior to and following culture is complete, which thereby finds, from the difference between the particle-size distributions of the two, the increased germ count.

In step S8, the processing unit 103 waits for a predetermined time T to pass. Since this timing changes according to the specimen, to prescribe a set figure would be difficult; but in the case of urine, for example, a period of approximately four hours is generally sufficient.

In steps S9 through S14, changes in block section data are sought for every block section created in step S4, and a process to determine the increase in germ count is executed.

First, in step S9, the processing unit 103 selects a block section to be processed from among a predetermined number of block sections. Generally, the block section to be processed is taken in sequence from(x=1, y=1).

In step S10, the processing unit 103 seeks the changes in the block section data for the block sections targeted for processing, by subtracting the block section data prior to culture from the block section data following culture.

In step S11, the processing unit 103 functions to determine whether or not the change in the block section data is less than predetermined values. If "yes," the process flow goes to step S12. If "no," process flow goes to step S13, which will be discussed below. An extremely minimal change in the block section data is considered to be no increase in the number of bacteria, since the procedure takes into consideration a margin of error in the measurement. In general, the predetermined values are determined empirically.

In step S12, the processing unit 103 establishes the increase in the number of bacteria to be zero for the block section data to be processed. Moreover, the processing unit 103 correlates the block sections and the increase in germ count and retains this data in the memory 102.

In step S13, for the block section that is the object of the process the change in block section data is the predetermined value or greater, and therefore the processing unit 103 assumes:(increase in germ count)=(change in block section data). Likewise as in step S12, the processing unit 103 correlates the block section and the increase in germ count and stores this data in the memory 102.

In step S14, the processing unit 103 determines whether or not the increase in germ count has been sought for all the block sections. If "yes," control proceeds to step S15. If "no," control returns to step S9, and the increase in germ count is determined for the next block section.

In steps S15 through S20, processing is performed in which the particle-size distribution prior to and following culture and the analysis results of the increased germs are displayed in order. It is not necessary to display all of these; only the information concerning the increased germs, for example, can be displayed. Moreover, various analytical results can be displayed, in response to commands received from a user.

First, in step S15, the processing unit 103 determines which particle-size distribution will be the object of analysis and display, that of germs pre-culture, post-culture, or increased. In the present embodiment, display is made in a pre-culture, post-culture, increased germ sequence.

In step S16, the processing unit 103 seeks the proportion of each of the block section data, with the block section with the largest block section data set at 100%. When the bacteria to be analyzed has increased, the processing unit 103 seeks the proportion of increase in the bacteria in each of the block sections, with the number of bacteria in the block section with the maximum increase in bacteria set at 100%.

In step S17, the processing unit 103 makes a determination to display the block sections wherein the block section data or the increase in germ count falls below the predetermined proportion. This is done because the particle-size distribution will be difficult to see and the characteristics of the increased germs will be difficult to determine if all the block sections are displayed. The below-described FIG. 21 through 28 show analytical results wherein the portions in which the percentage of the block section data or of the increase in germ count is 10% or less are taken to be the display portions.

In step S18, the processing unit 103 divides the proportions of the block section data or the increase in germ count into predetermined levels, and selects predetermined display colors, which differ according to the level, for each of the block sections within the portion to be displayed. The below-described FIG. 21 through 28 are examples of analytical results that are displayed using colors that differ with each of five levels: 0 to 2%; 2 to 4%; 4 to 6%; 6 to 8%; and 8 to 10%.

In step S19, the output control unit 104 outputs the portion to be displayed to the output unit, using the established display colors. Accordingly the analytical results illustrated in FIG. 21 through 28 are displayed in the output unit.

In step S20, the processing unit 103 determines whether or not all pre- culture, post- culture, and pre-/post-culture analytical results have been displayed. If "yes," the routine ends. If "no," the process flow returns to step S15, and the analytical results not yet displayed will be displayed.

Embodiments

An explanation will be given of measurement of microorganisms in a sample performed using a flow cytometer and the signal-processing unit.

(1) Counting the Number of Microorganisms (1-1) Culture and Counting urine was chosen for the specimen. Testing for bacteria in urine is widely performed on a clinical basis for the diagnosis of urinary tract infections such as urocystitis and nephropyelitis.

A generally used liquid culture for bacteria, a heart infusion bouillon (manufactured by Nissui), was used. The specified directions for using the product were followed. After the product was heated and melted, it was sterilized by means of high pressure steam.

First, two test tubes containing 2 ml of the culture solution were used. The two test tubes containing the culture sample were prepared by adding 100 $\mu$l of a urine specimen to each test tube and agitating. The number of microorganisms was counted by means of a flow cytometer, as will be explained below, in one of the culture samples, without performing culture. The other culture sample was placed in an incubator at 37° C.; after it was cultured for four hours, the number of microorganisms was counted in the same way, by means of a flow cytometer.

The counting of the microorganisms by the flow cytometer was conducted in the following way. The amount of the sample to be analyzed by the flow cytometer was set at 0.8 $\mu$l. The forward scattered light was detected by the flow cytometer, and the detected light was input into the signal-processing unit 10; by so doing the intensity of the forward scattered light over the duration of the emission the forward scattered light was measured. The measurement results of the culture sample with the culture was established as the first particle-size distribution, and the measurement results of the culture sample prior to the culture was established as the second particle-size distribution. The difference between the first particle-size distribution and the second particle-size distribution was sought, as the final particle-size distribution of the culture sample.

Figure 7:
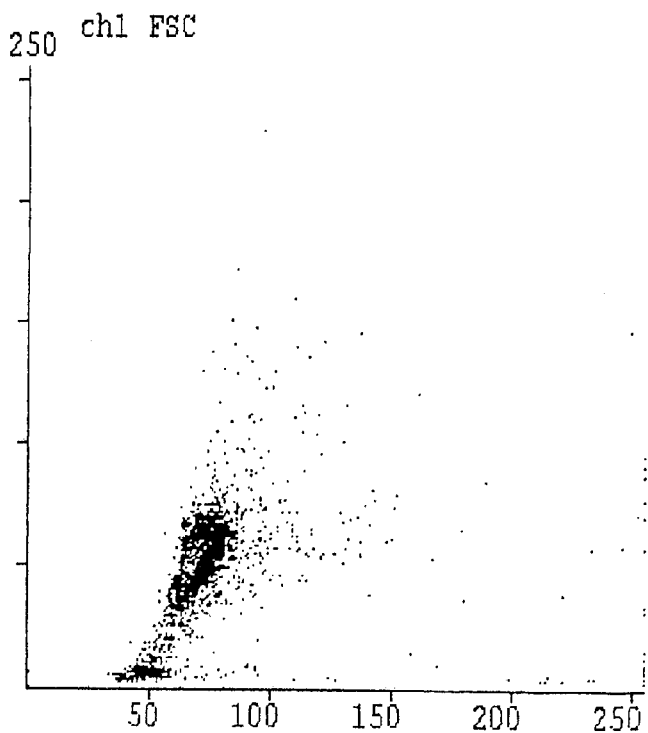
FIG. 7 is particle-size distribution graph prior to the urine sample culture to which FIG. 6 relates.

FIG. 6 and FIG. 7 indicate the measurement results of the first and second particle-size distributions of the specimen. The horizontal axis represents the duration, FSCW (forward scattered light width), of the scattered light pulse. The vertical axis represents the intensity of the scattered light FSC. 100 ch on the vertical axis of the particle-size distribution shown in FIG. 6 and FIG. 7 corresponds to a particle diameter of approximately 1 $\mu$m. As many as 25,676 particles were found to have grown from the particle-size distribution in FIG. 6 and FIG. 7. The increase in number of particles was obtained by seeking the difference in the data amounts (the plot amounts in each of the particle-size distributions) prior to and following culture.

(1-2) Comparison of Accuracy with Conventional Methods

Next, a comparison was made between the number of microorganisms found in the particle-size distribution prior to and following culture and the number of microorganisms cultured and counted in the traditional agar plate medium.

The sample was arranged and cultured in the same manner as was stated in (1-1) above, and the particle-size distribution was measured. The count of the microorganisms was sought, based on the measurement(hereafter referred to as "the present method").

The culture and the measurement conducted on the agar plate medium, which represented the contrasting control medium, was performed in the following way.

First, Uricult E® (manufactured by Orion Diagnostica Danmark A/S of Denmark), which is generally used in a test to find microorganisms in urine, was utilized in agar plate media. These culture media comprised CLED, MacConkey and Enterococcus media. The handling directions for the products were followed, and urine samples were smeared onto the surface of the culture media. They were cultured at 37° C. for 24 hours. In the evaluation, the density of the colonies was visually compared with a contrast table that was supplied, and the germ counts in the urine was sought.

Figure 8:
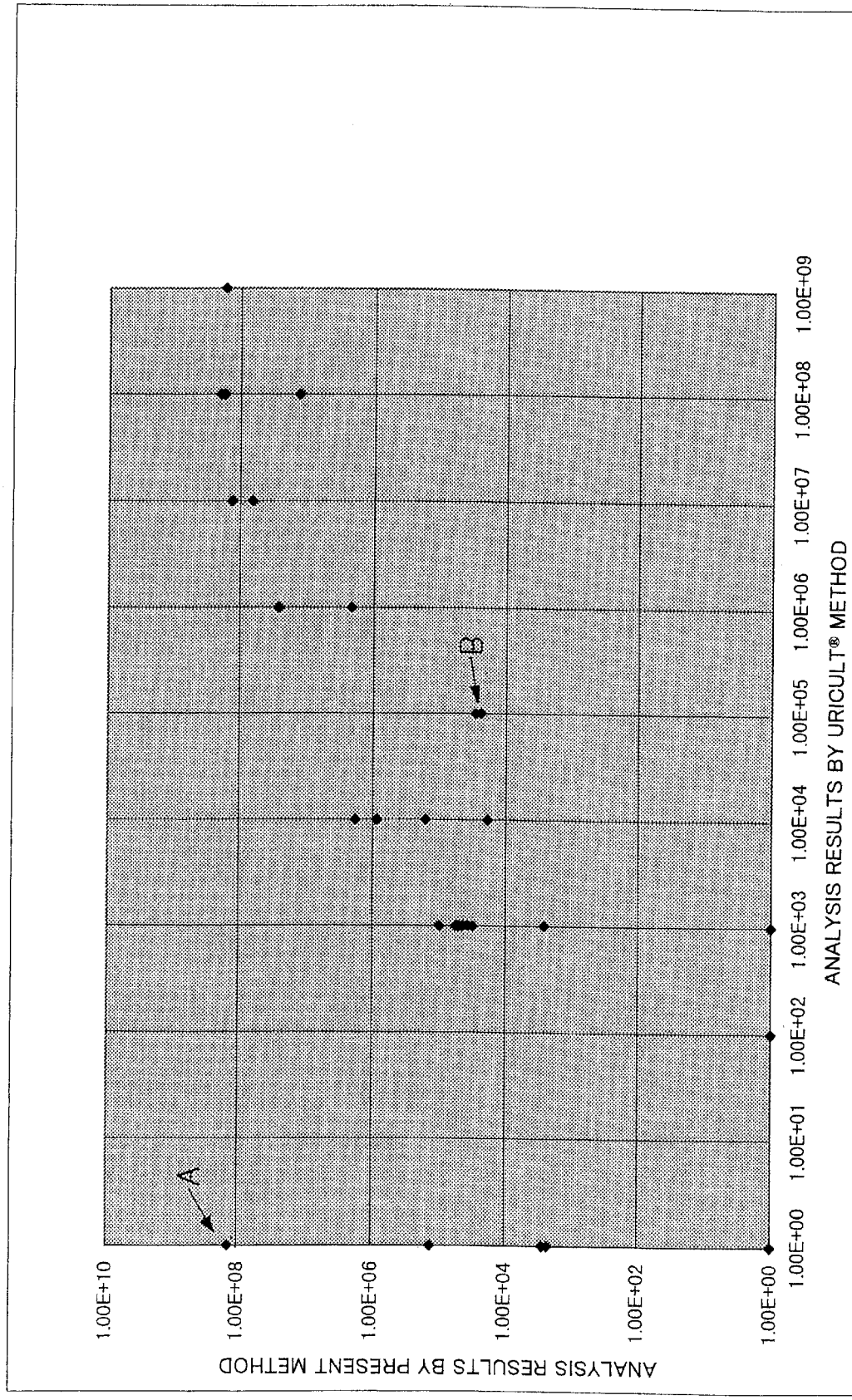
FIG. 8 is a graph comparing measurement results by the Uricult E® method with results of the method in accordance with the present invention.

The Uricult E® method and the present method were performed on 40 specimens. The results of the measurements are shown in FIG. 8. FIG. 8 shows the measurement results for the bacterial count that were performed by the Uricult E® and the present methods.

In the Uricult E® method, a bacterial count of $10^5$/ml or more was considered to be positive(bacilluria); a definitive determination was reserved, and the specimen was considered to possibly be borderline positive, if the bacterial count was $10^4$/ml. A comparison was made between the measurement results using the present method and 16 specimens that presented a reading of $10^4$ unit/ml or more when the Uricult E® method was used. The results of the measurements using the present method showed that in each of the 16 specimens, there was a similar reading, a count of $10^4$ unit/ml or more. Moreover, the difference in the value of the measurement was within the range of a single figure. From these results, a good correlation was shown between the Uricult E® method and the present method.

Next, a re-test was performed on a specimen (FIG. 8, Arrow A) that produced a negative result under the Uricult E® method and a high positive reading in the present method. A dissolved area was present on the surface of the Uricult E® medium. This was caused by overcrowding of the bacterial colony. Thus, in the case of this specimen, an erroneous negative reading was produced in the Uricult E® method, when the bacterial cells were, in fact, increasing.

Figure 9:
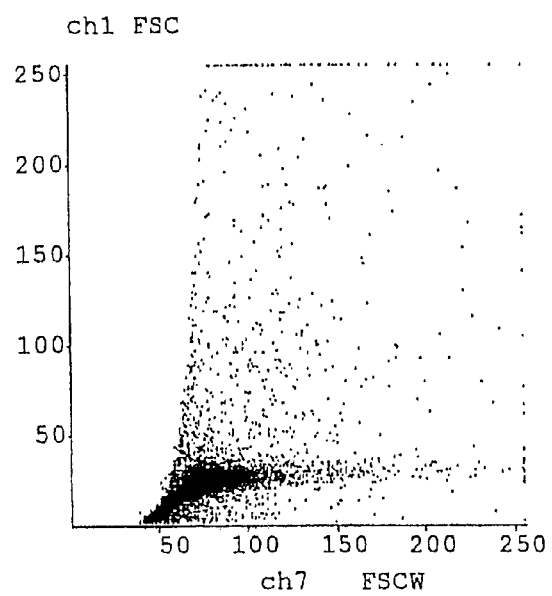
FIG. 9 is a post-culture particle-size distribution graph for Streptococci in a sample.
Figure 10:
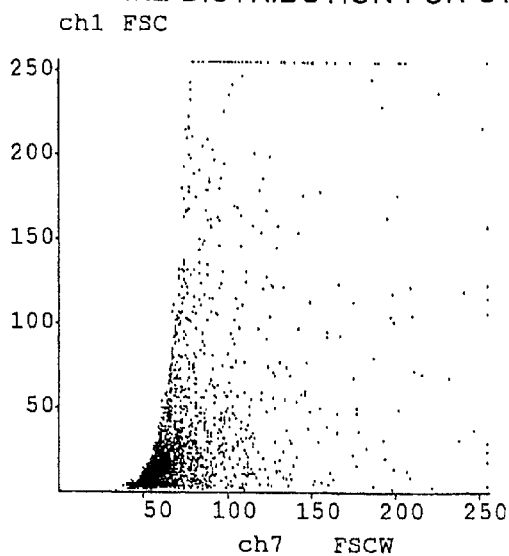
FIG. 10 is a pre-culture particle-size distribution graph for Streptococci in the FIG. 9 sample.
Figure 11:
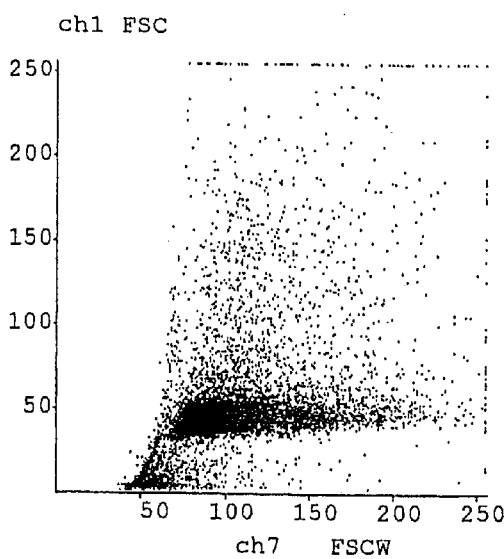
FIG. 11 is a post-culture particle-size distribution graph for Streptobacilli in a sample.
Figure 12:
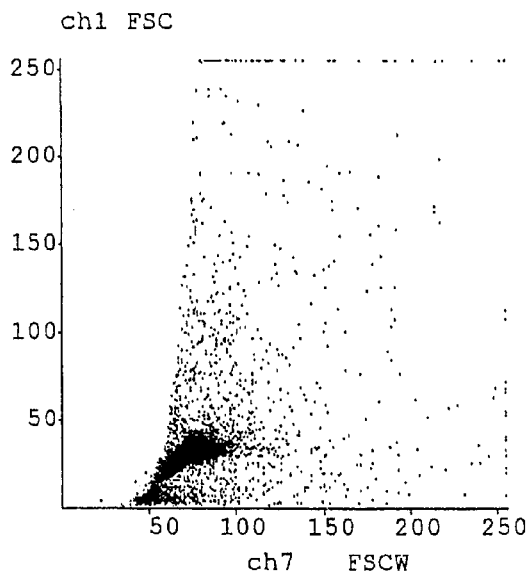
FIG. 12 is a pre-culture particle-size distribution graph for Streptobacilli in the in FIG. 11 sample.

Next, two specimens (FIG. 8, Arrow B) were examined in which the present method produced a lower reading than that of the Uricult E® method. The figures showing the particle-size distribution (FIG. 9, FIG. 11) following culture of both specimens show, in both cases, the particle-size distribution extending as the duration of the emission of the scattered light grows longer. This particle-size distribution is not apparent in the particle-size distribution graphs prior to culture (FIG. 10, FIG. 12). Thus, these represent particle-size distributions that increased as a result of the culture. These culture samples were examined in further detail by means of a microscope. It was found that, in both specimens, the bacteria had increased in linked formation. Moreover, when the bacterial types were examined, they were shown to be Streptococcal Enerococcus erogenes, as shown in FIG. 9 and 10, and Streptobacillal Pseudomonas, as shown in FIG. 11 and 12.

From these findings, it was shown that the following causes were responsible for the discrepancies in the measurement results of the Uricult E® method and the present method. The Streptobacilli and the Streptococci increase in chain-link (concatenated) formation. The flow cytometer, however, detects the concatenated clumps of multiple counts of bacteria as a single particle. Thus, even when there was an increase in the bacterial count, the flow cytometer was unable to detect the actual increase in the bacteria, since they were concatenated.

Since the Streptobacilli and the Streptococci form long chains, there is little change in the intensity of the scattered light; the duration of the emission of the scattered light is prolonged, however, according to the length of the concatenated bacteria. Therefore, through the detection of the signal showing that the duration of the emission of the scattered light is long, it is possible to detect the increases in the Streptobacilli and the Streptococci, which would go undetected if an examination is performed only on the intensity of the signal.

In concrete terms, when a bacterial count in excess of a predetermined amount is detected in a region in which the duration of the scattered light emission is more than 90 ch, for example, a positive determination can be made, showing the presence of the Streptobacilli or Streptococci. Moreover, by multiplying the signal from that region with a coefficient corresponding to the bacterial count of concatenated bacteria and in proportion to the duration of the scattered light emission, it is possible to estimate the increase in the number of microorganisms.

Through the results of the examinations presented above, it was found that the present method possesses a good correlation with the conventional Uricult E® method and that good measurement results can be presented in a far shorter culture period than that required by the conventional methods.

By using a selective medium for the type of culture solution, it is possible to identify the variety of the microorganism, by means of the same aforementioned process. Since the culture period is brief, it is possible to conduct a detailed study of the microorganisms under various culture conditions, in a short time.

Moreover, the relationship between growth forms and the particle-size distribution graphs was examined for various microorganisms other than the Streptobacilli and Streptococci.

Other species of bacteria, in addition to the Streptobacilli and Streptococci, which manifest collective growth, are the Staphylococci. Samples of two types of the Staphylococci were used, and in each case, the bacteria were cultured in the same manner as was done in (1-1). A flow cytometer was used to detect the scattered light and measurement was conducted on the particle-size distribution by means of the signal-processing unit. The particle-size distribution graphs are represented by FIG. 17 and 18. Unlike the concatenated bacteria, the particle-size distribution in the present case indicated a particle-size distribution that extended in a narrow and long formation in the direction of increasing scattered light intensity. The Staphylococci manifest growth in collective clusters. Accordingly, the diameter of the bacterial clusters grew with the increase in the bacteria, and this increased the intensity of the scattered light.

A similar investigation was conducted on the particle-size distribution of the Streptobacilli, species of bacteria that do not form collective clusters when multiplying. Their particle-size distribution graphs are shown in FIG. 15 and FIG. 16. These did not show a particle-size distribution formation that extended with a greater intensity or longer emission time of the scattered light signal. This showed that the intensity and the duration of the emission of the scattered light signal remained unchanged and was manifested at points below predetermined values, because the bacteria were in a scattered formation, even when they multiplied.

Figure 29:
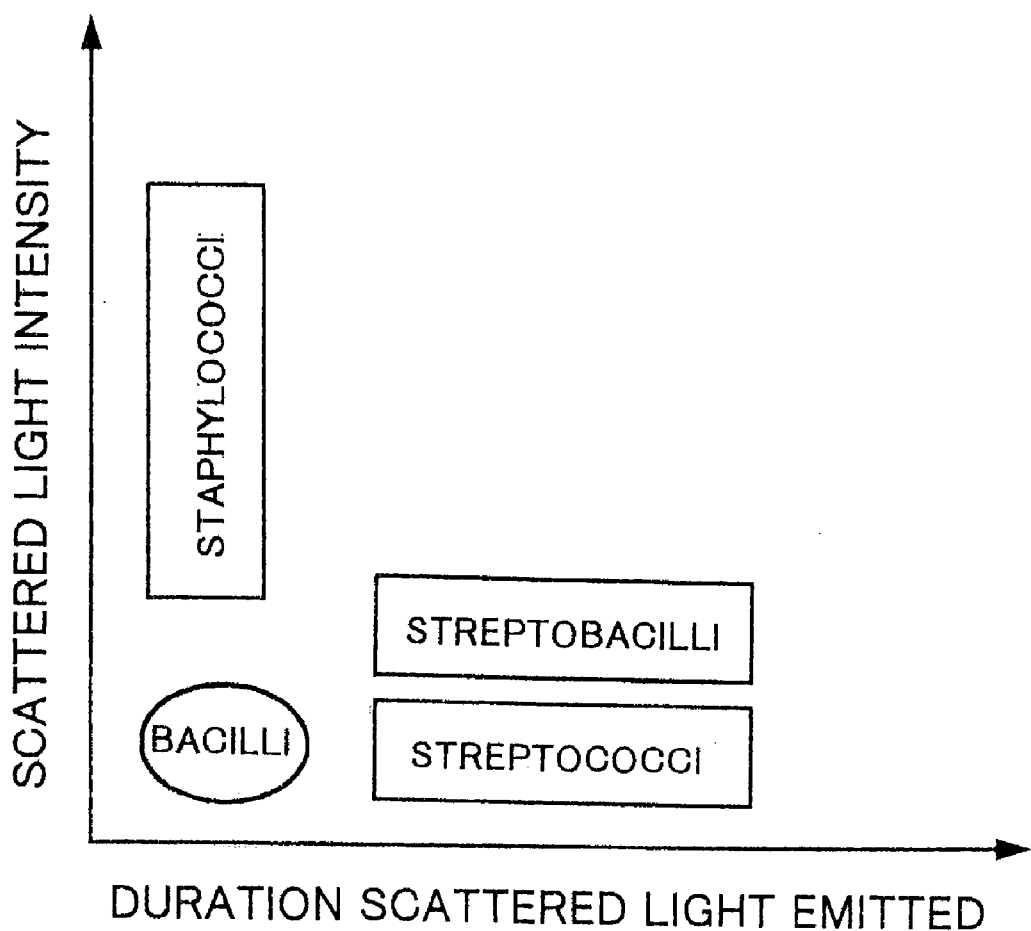
FIG. 29 is a reproduction diagram depicting particle-size distribution differences according to bacteria type: Staphylococci, Streptococci, Streptobacilli and Bacilli.

From these investigations, it was found that, since the flow cytometer considered a collective bacterial group to be a single particle, the readings for the Streptobacilli, the Streptococci and the Staphylococci manifested an increase that was lower than the actual growth. Moreover, it was found that, since the growth forms of the Streptobacilli, the Streptococci, the Staphylococci and the Bacilli were different, it was possible to identify the various forms of the bacteria, based on the particle-size distribution of the bacteria that manifested the growth. It was shown that, of these, it was not possible to identify the Streptobacilli and the Streptococci solely by measuring the intensity of the scattered light, since they were not sufficiently different from the Bacilli, which has a singular scattered light intensity. By measuring the double parameters of the intensity and the duration of the emission of the scattered light, it was possible to distinguish among Staphylococci, Streptococci, Streptobacilli and Bacilli species. FIG. 29 shows a model representation of the distinctions in the particle-size distribution among the four varieties of bacteria.

Specifically, an alert for the presence of Streptobacilli was issued, for example, when bacteria was detected in excess of a predetermined amount in a region in which the intensity of the scattered light was 90 ch or less, and the duration of the emission of the scattered light 90 ch or more. An alert was issued for the presence of the Staphylococci when bacteria were detected in excess of the predetermined amount in a region in which the intensity of the scattered light was 50 ch or more and the duration of the emission of the scattered light was 80 ch or less. Since the particle-size distribution extends in accordance with the growth of both Streptobacilli and Staphylococci, in judging just from the number of individual regions, the form of the particle-size distribution can be observed.

In addition, since the collective bacteria causes changes in the particle-size distribution, it is possible to estimate the increase in the number of bacteria itself, by multiplying the signals of that region with the coefficient for the grouped bacteria, in proportion to the intensity of the scattered light or the pulse duration.

Figure 13:
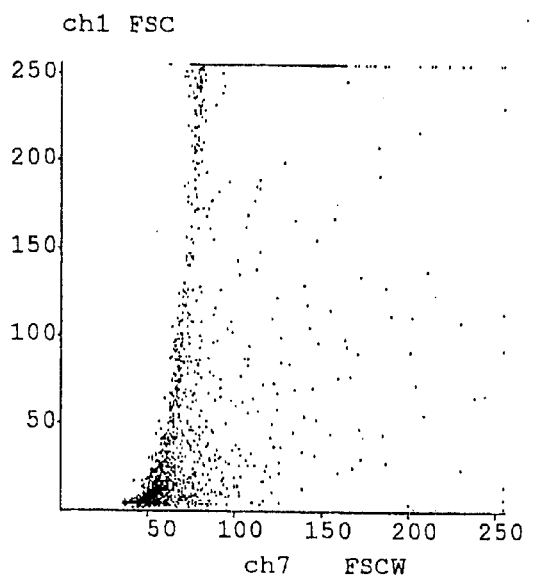
FIG. 13 is a post-culture particle-size distribution graph for yeast fungi in a sample.
Figure 14:
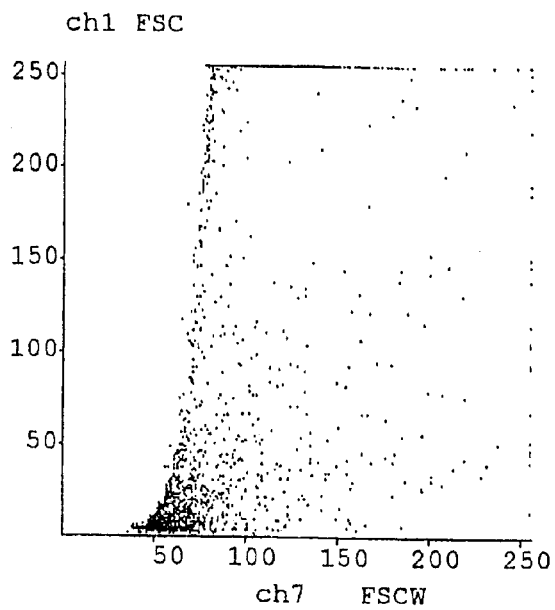
FIG. 14 is a pre-culture particle-size distribution graph for yeast fungi in the FIG. 13 sample.

The results for the measurement of the particle-size distribution for the yeast fungi are indicated below. FIG. 13 and 14 represent the particle-size distribution graphs for yeast fungi. Since signals appear when the intensity of the scattered light exceeds 250 ch, the particle size is not shown in this figure. Because yeast fungi are large, at 3~5 μm, the scattered light intensity also increases.

(2) Classification of the Microorganisms

An analysis of the measurement results was conducted by the signal-processing unit in connection with the present embodiment, in order to classify the microorganisms. The measurement results and analysis results will then be explained.

The following bacteria were used as target cultures.

The bacteria listed below can be detected in urine, and they are targeted for examination when bacterial tests are conducted with urine specimens.

| | |
|---|---|
| Bacilli (1) | Escherichia coli |
| Bacilli (2) | Pseudomonas aeruginosa |
| Staphylococci (1) | Staphylococous aureus |
| Staphylococci (2) | Staphylococous epidermidis |
| Streptococci (1) | Enterocococus faecalis |
| Streptococci (2) | Streptococous agalactiae |
| Streptobacilli | Pseudomonas |
| Yeast fungi | Candida glabrata |

These bacteria were cultured under the same conditions as described in (1-1). A flow cytometer was used to detect the scattered light, and a signal-processing unit was used to measure the particle-size distribution. The culture period in this experiment, however, was two hours, instead of the previous four hours. FIG. 15 through 20 represent the particle-size distribution prior to and following culture of each bacterial form. FIG. 15 shows Bacilli (1); FIG. 16 shows Bacilli (2); FIG. 17 shows Staphylococci (1); FIG. 18 shows Staphylococci (2); FIG. 19 shows Streptococci (1); and FIG. 20 shows Streptococci (2). The particle-size distribution was sought for each bacterial form. The particle-size distribution of the Streptobacilli is as shown in FIG. 11 and 12. The particle-size distribution of the yeast fungi is as shown in FIG. 13 and 14.

In each of FIG. 15 through 20, a comparison was made between FIG. (a) and FIG. (b) in order to find in which region in the particle-size distribution graph the bacteria were increasing. These changes are difficult to find when there are no changes that are significant. Thus, as mentioned above, analytical processing was conducted in which the changes in the particle-size distribution prior to and following culture were sought for each block section of the particle-size distribution graph, and block sections in which the change proportion fell within the prescribed range were displayed.

The results of the analysis are represented in FIG. 21 through 28. The analytical results are shown in a graph. The particle-size distribution graph was divided into 256×256 block sections, and the number of particles contained in each block section was calculated; the largest number of particles was established as 100%, and the block sections that were 10% or less of this were displayed on the graph, with different colors for each prescribed level.

Figure 22A:
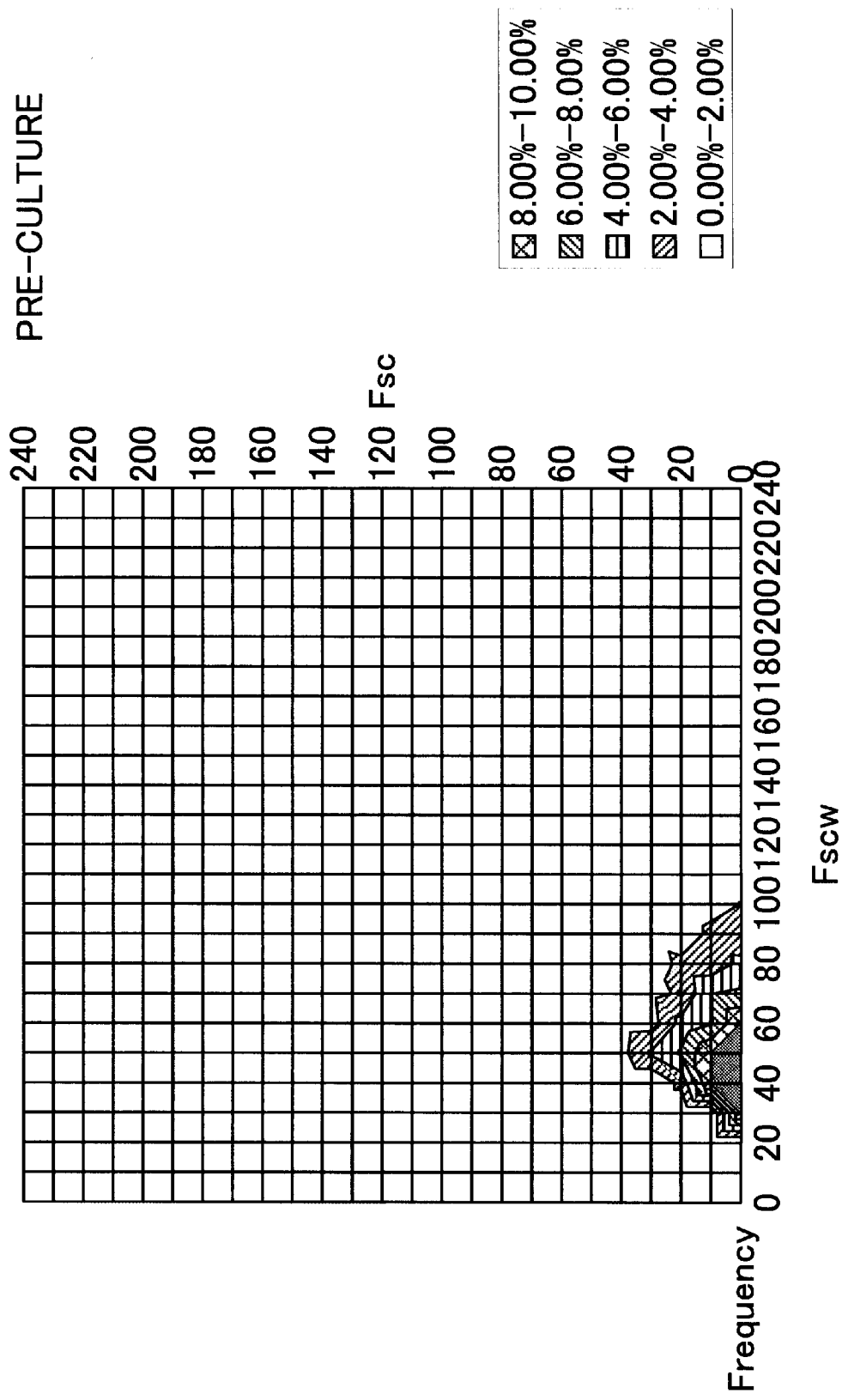
FIG. 22 graphs particle-size distribution assay results Bacilli (2)
Figure 22B:
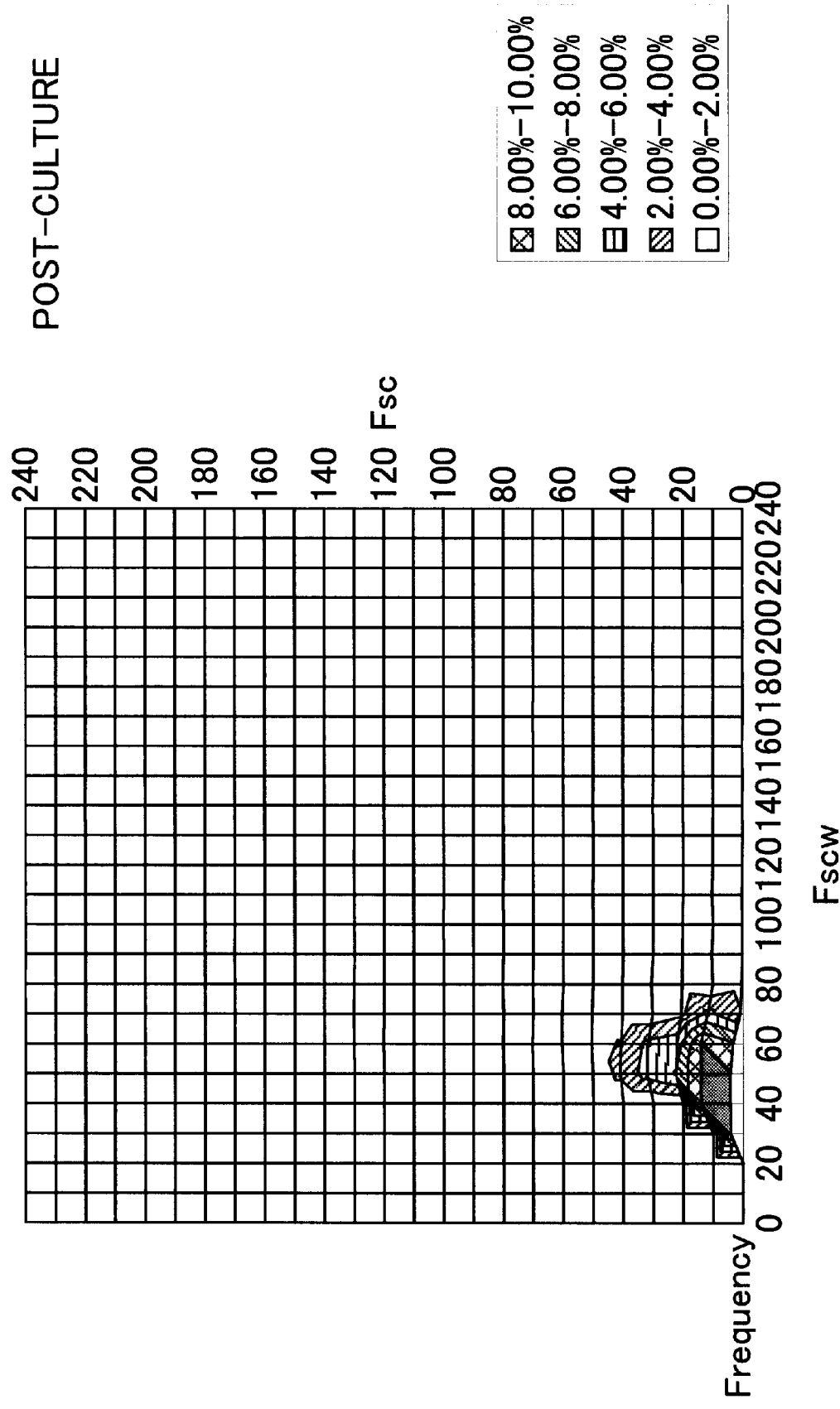
Figure 22C:
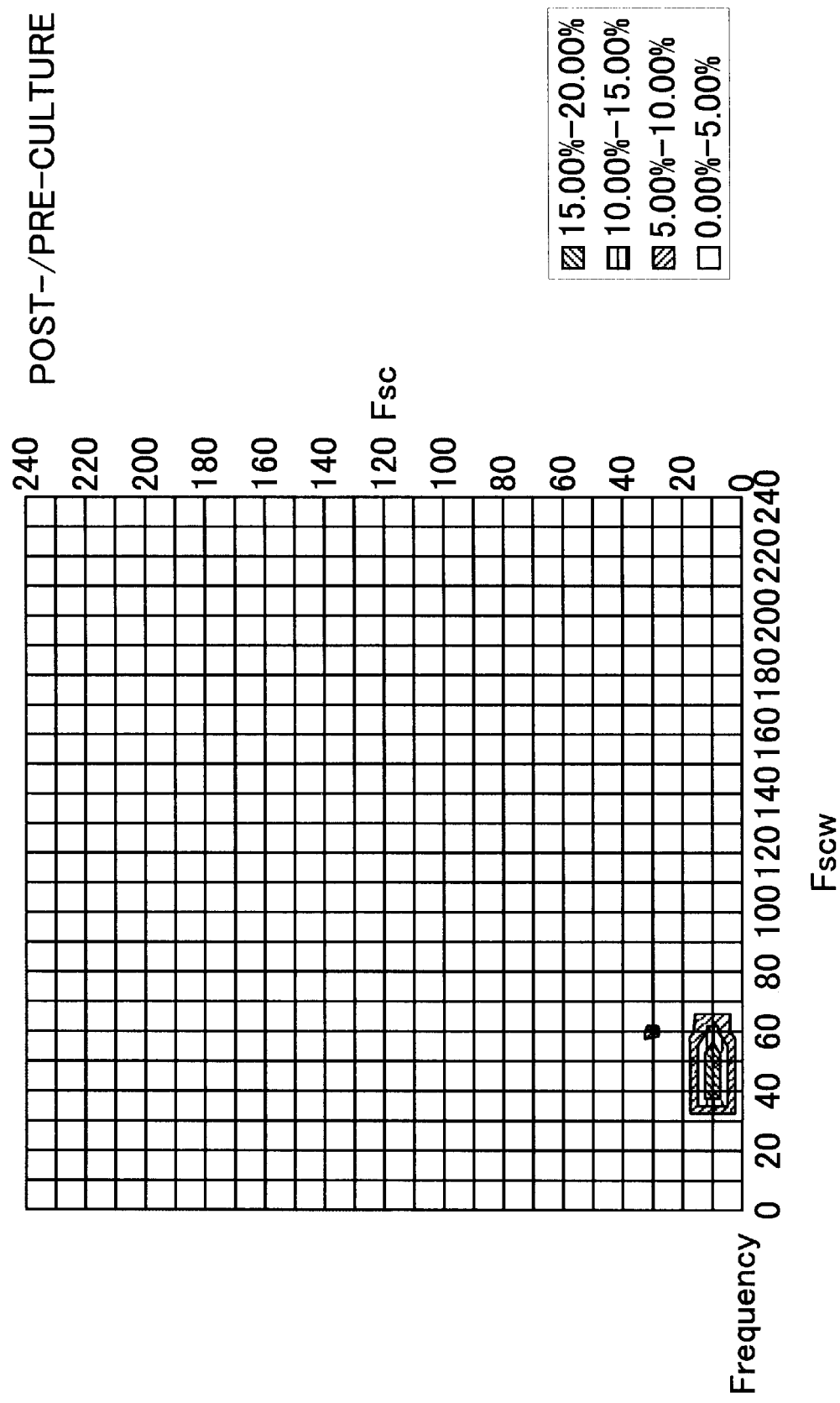

FIG. 21 and FIG. 22 present the analytical results prior to culture and following culture, as well as changes in particle-size distribution for Bacilli (1) and (2). The range for the intensity of the scattered light for Bacilli (1) is roughly 10 to 80 ch. The intensity of the scattered light for Bacilli (2) is in the range of 0 to 20 ch. The duration of the light pulse for the scattered light in the case of Bacilli (1) is in a range of approximately 40 to 90 ch and in the case of Bacilli (2) is short, in a range of 30 to 70 ch. There was a slight difference in the position of the particle-size distribution, depending on the type of Bacilli, but the particle-size distribution stayed together and did not extend far. In other words, it was shown that the Bacilli did not formulate collective groups when it increased in number. Moreover, it was indicated that the Bacilli (2) were a small-scale Bacilli with particles with a small diameter.

Figure 23A:
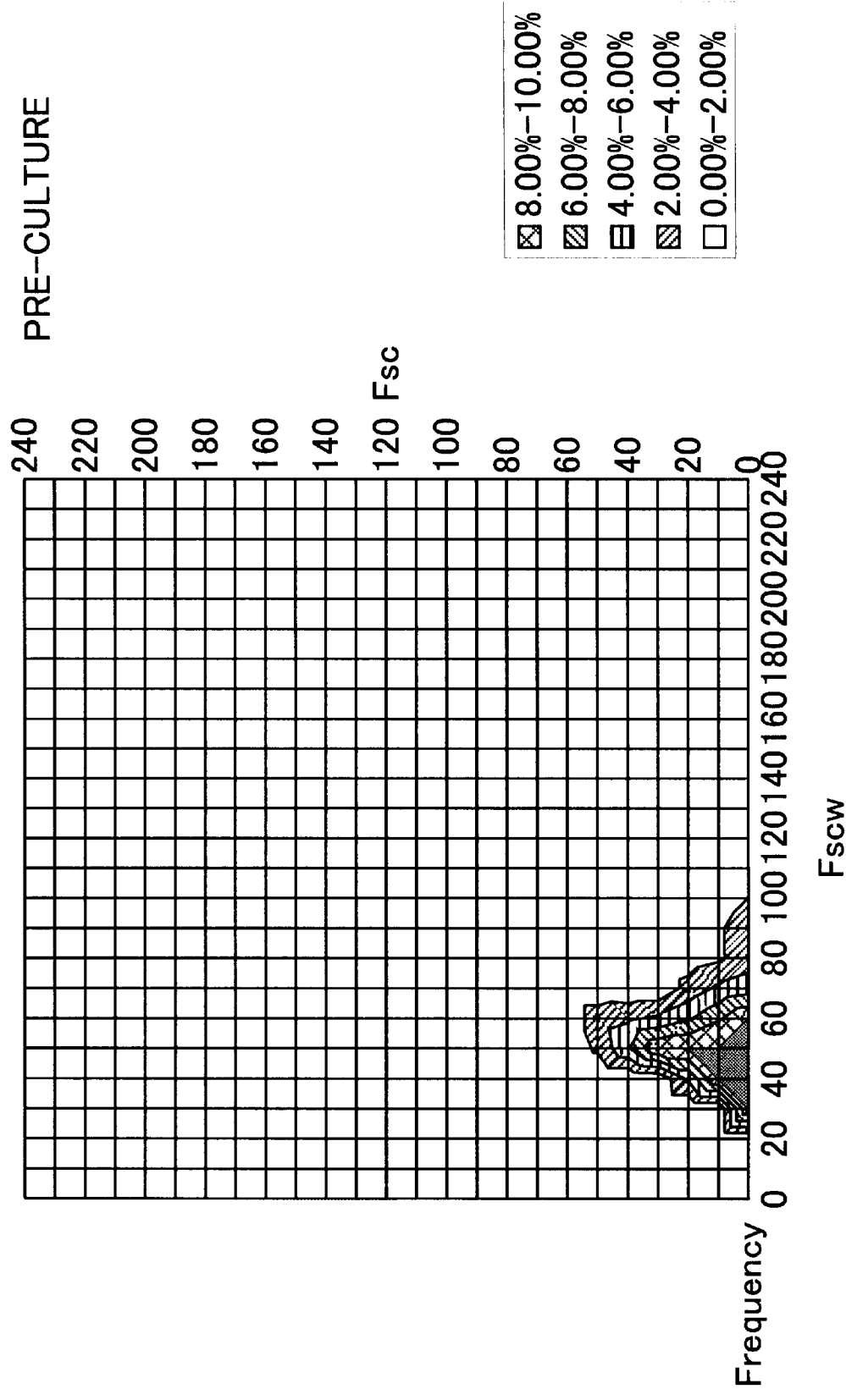
FIG. 23 graphs particle-size distribution assay results Staphylococci (1)
Figure 23B:
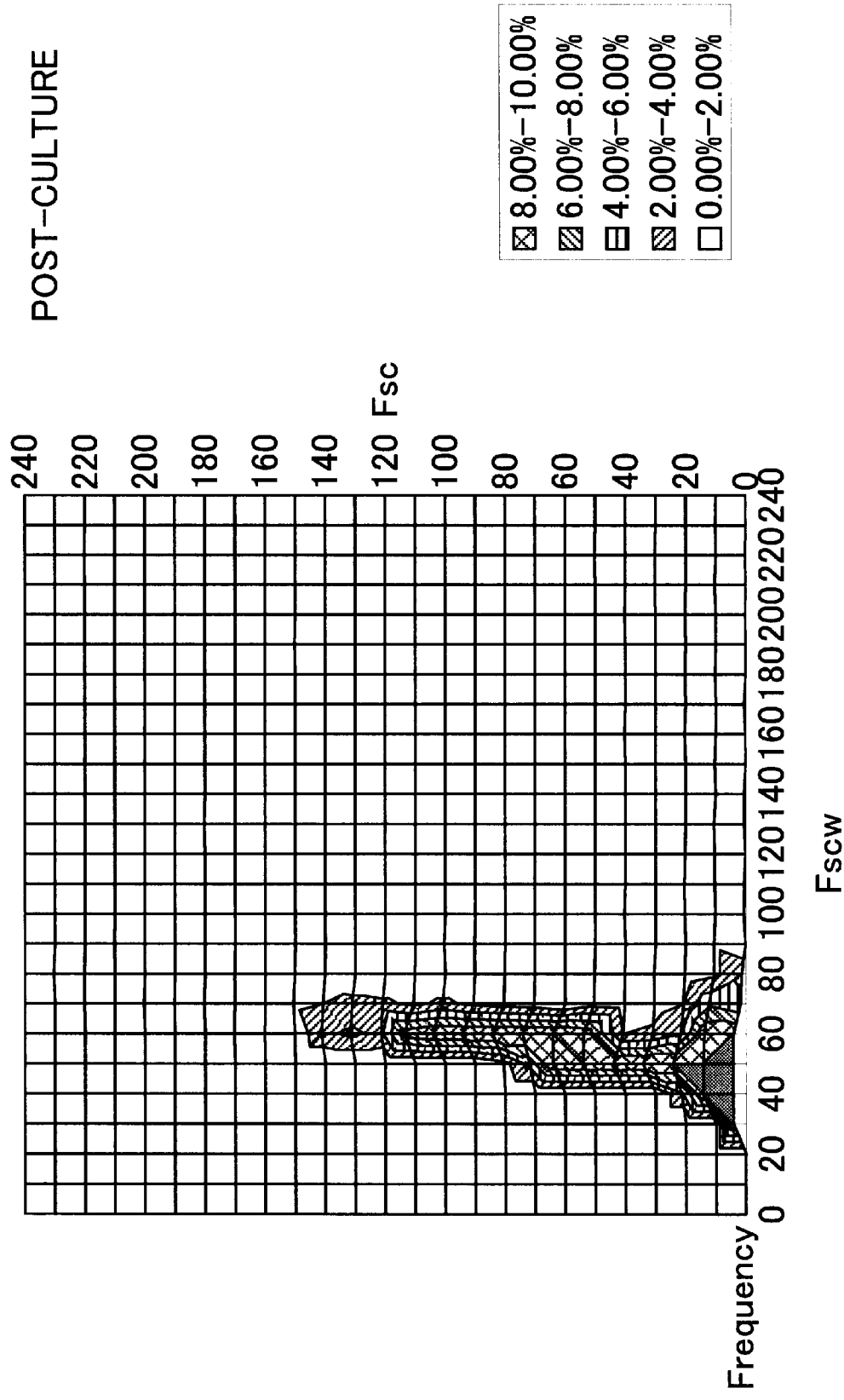
Figure 23C:
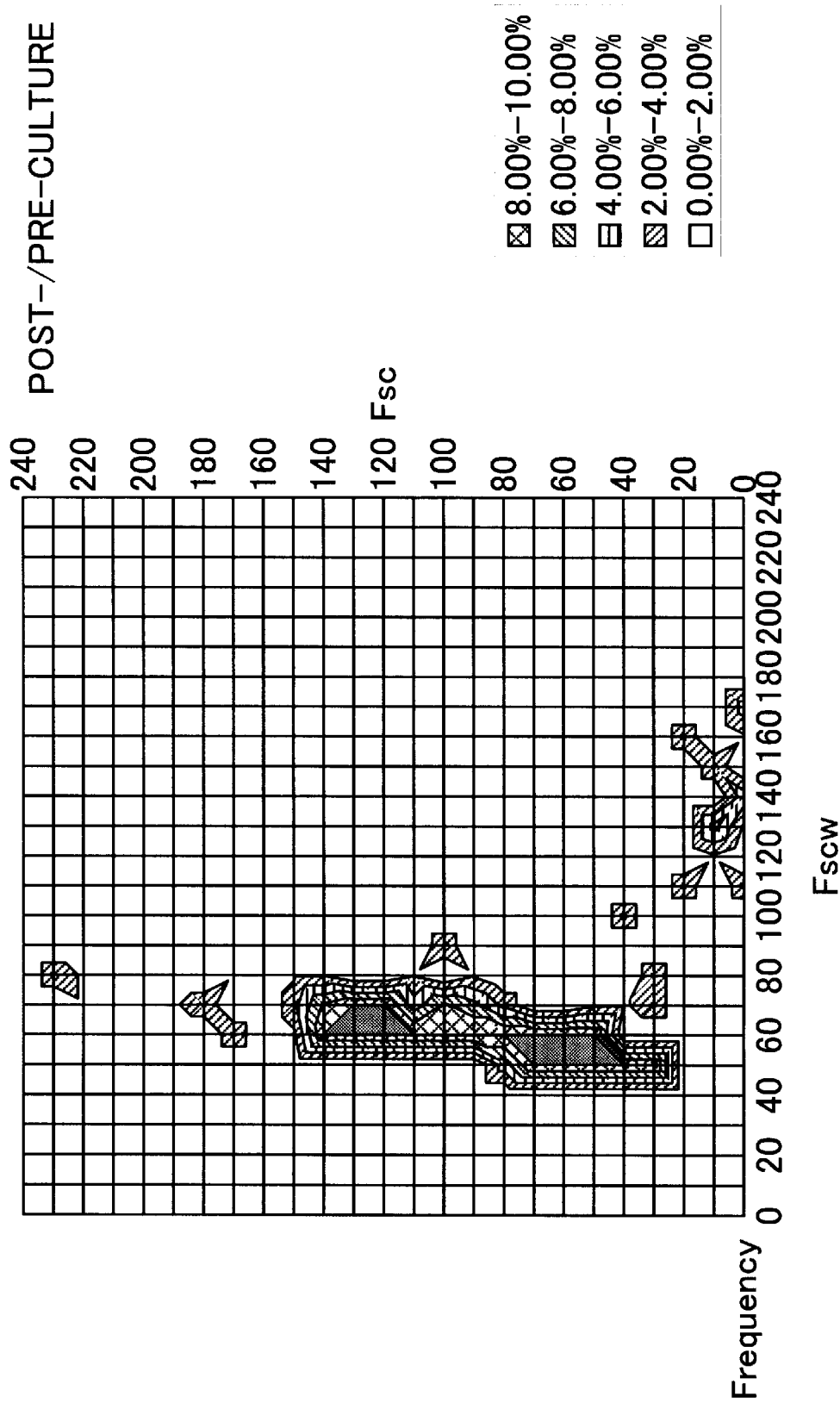
Figure 24A:
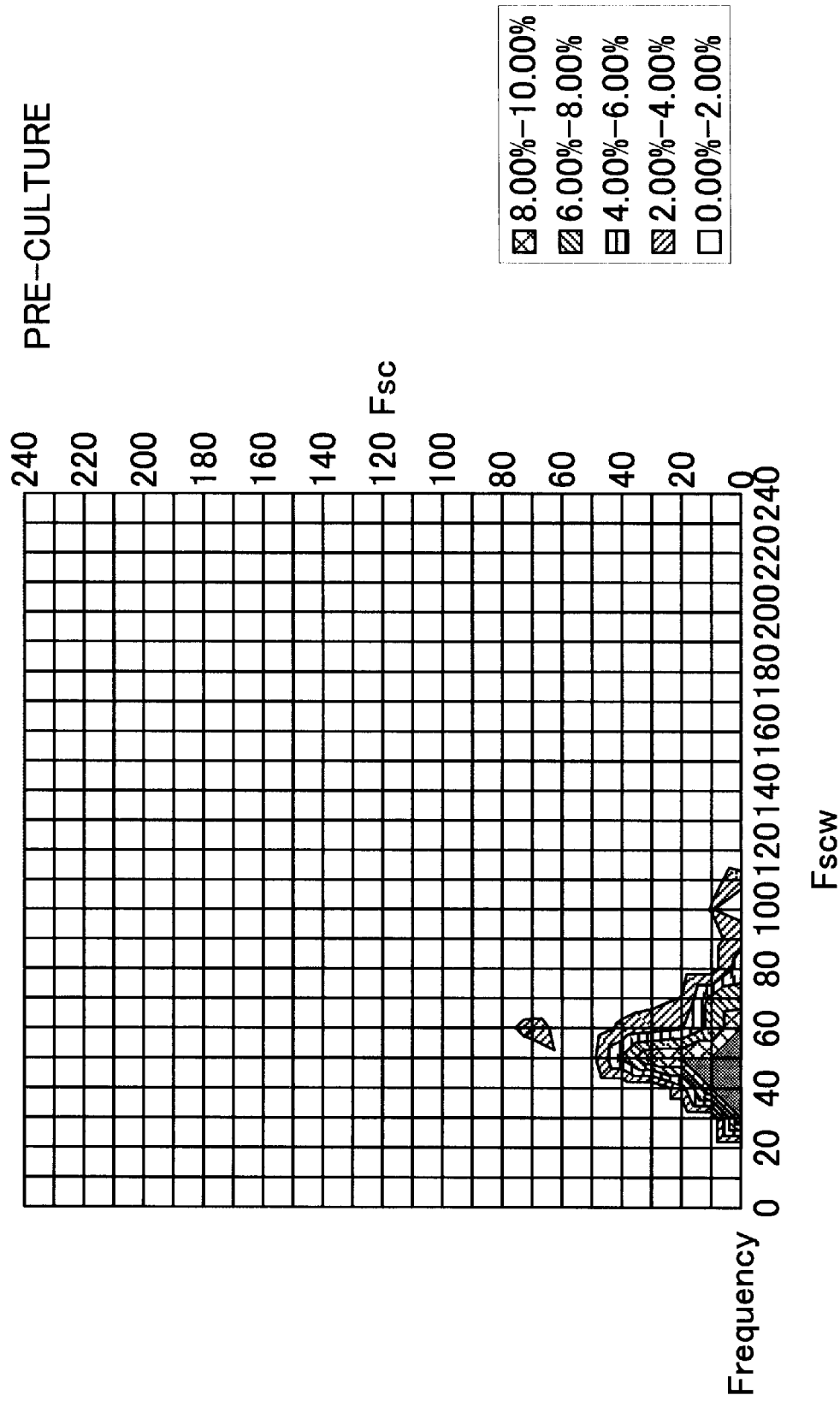
FIG. 24 graphs particle-size distribution assay results Staphylococci (2)
Figure 24C:
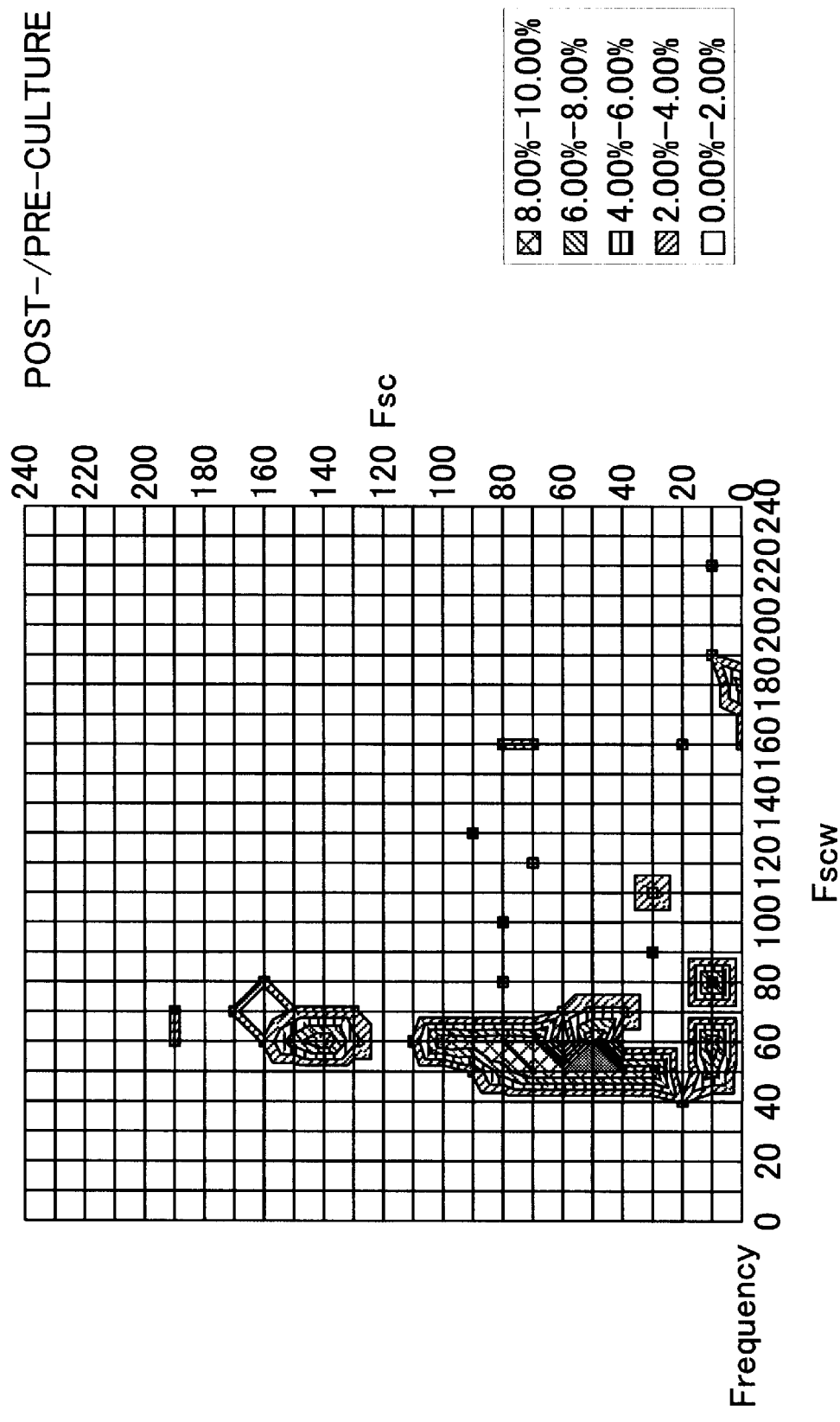

FIG. 23 and 24 are analytical results showing the bacteria prior to and following culture and changes in the particle-size distribution for the Staphylococci (1) and (2). Since the targeted culture is the Staphylococci bacteria, the intensity of the scattered light of the increased bacteria extends over a wide range. For example, with the Staphylococci (1), the intensity of the scattered light of the increased bacteria ranges primarily from 20 to 190 ch. In the case of the Staphylococci (2), the intensity of the scattered light in the increased bacteria primarily ranges from 0 to 160 ch. The duration of the emission of the scattered light, however, ranges from 40 to 90 ch, and it increases as the intensity of the scattered light increases. In other words, this shows that the bacteria increase in cluster formation and not concatenated.

Figure 25A:
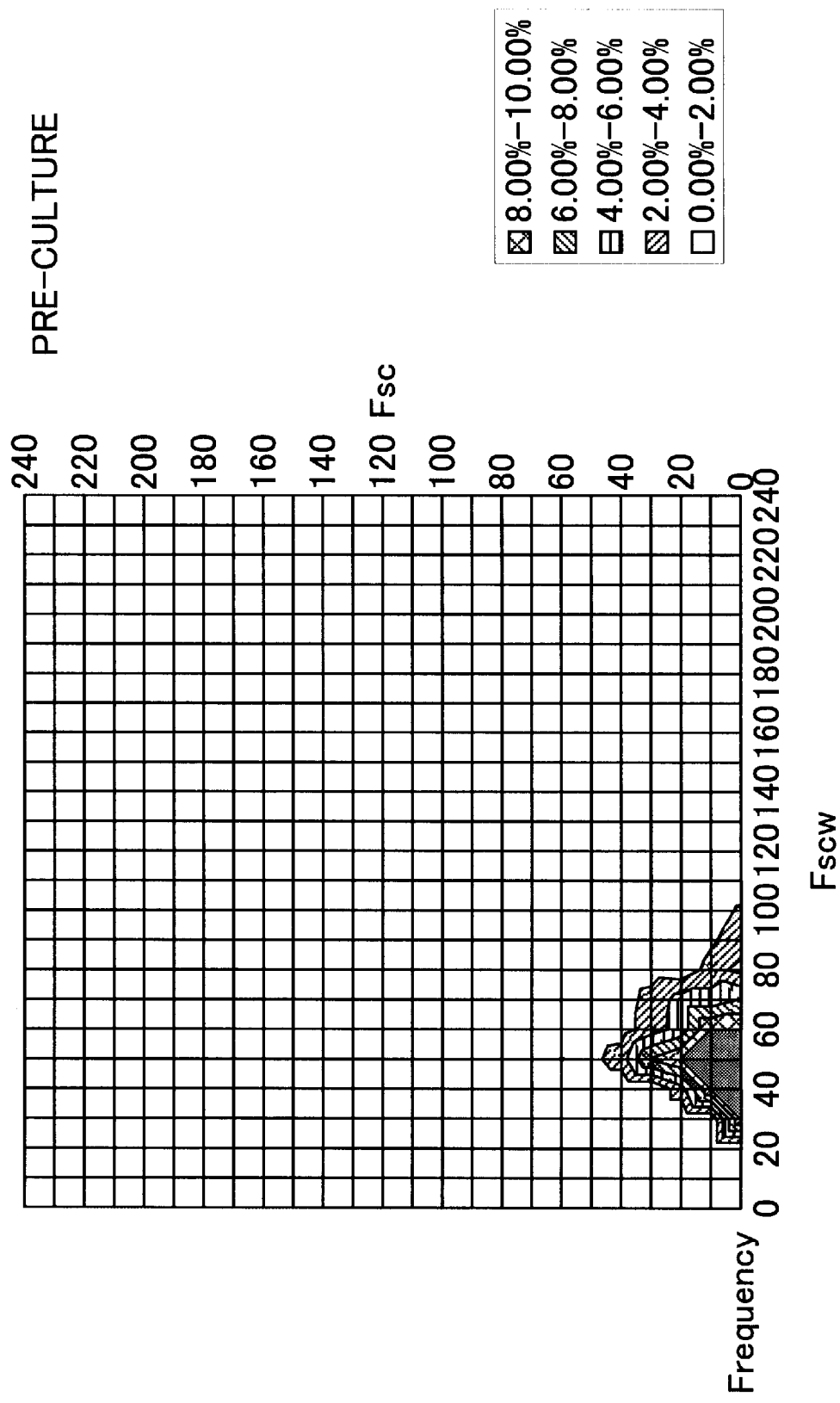
FIG. 25 graphs particle-size distribution assay results Streptococci (1)
Figure 25B:
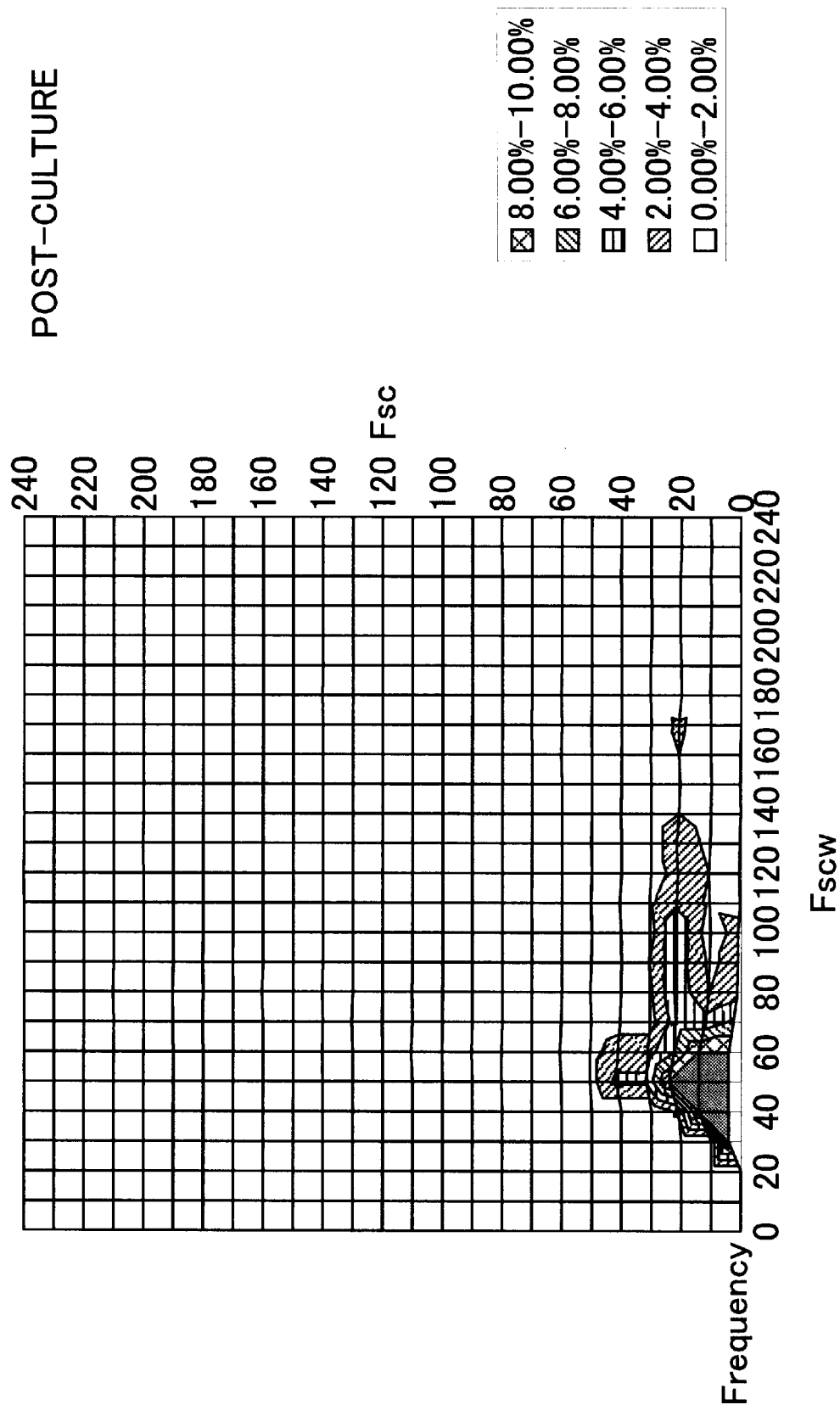
Figure 26A:
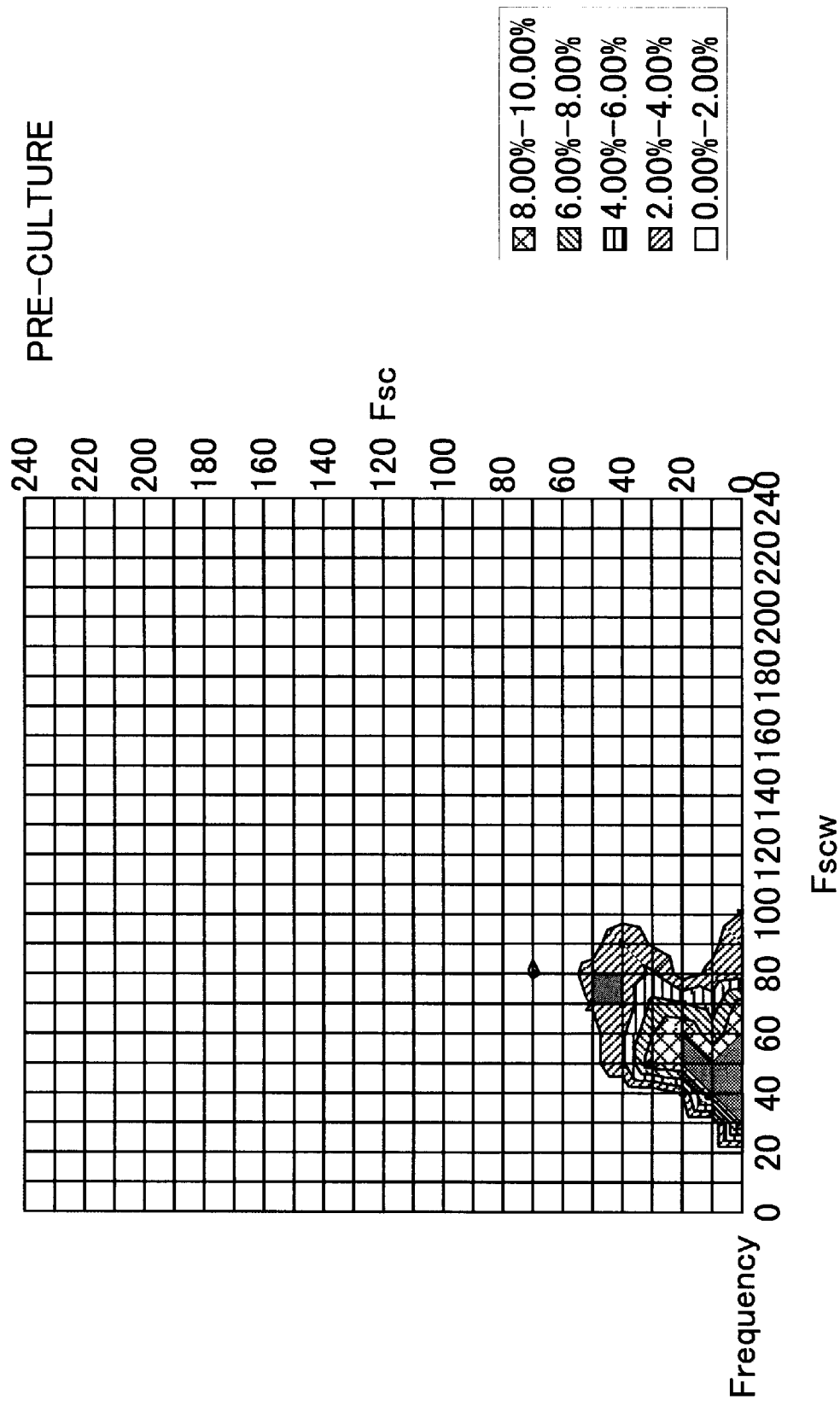
FIG. 26 graphs particle-size distribution assay results Streptococci (2)
Figure 26B:
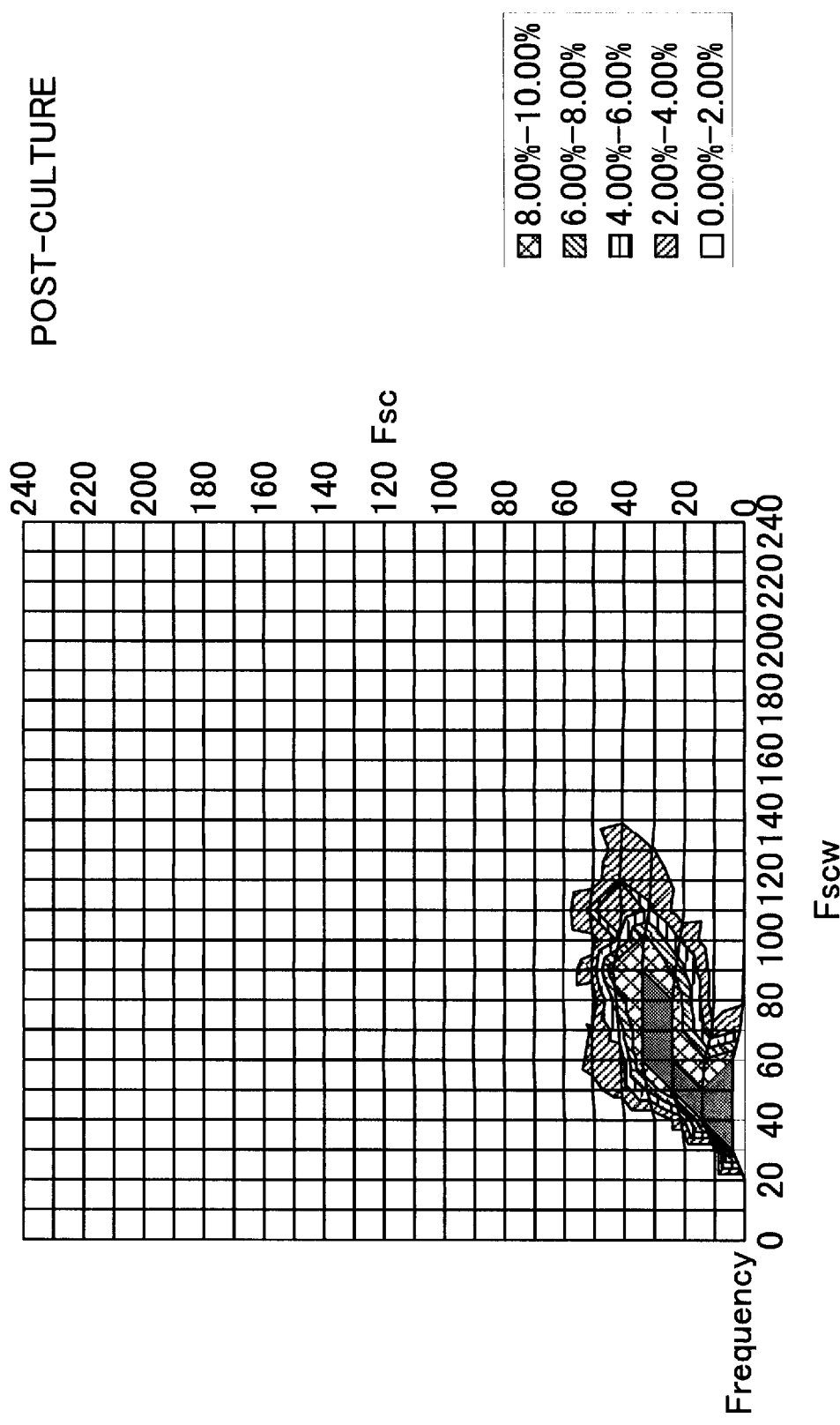

FIG. 25 and 26 represent the analytical results of the bacteria prior to and following culture, and they indicate the changes in particle-size distribution for Streptococci (1) and (2). Since the targeted culture is bacteria with chain-link formation, the intensity of the scattered light for the increased bacteria is contained within a small range, primarily from 0 to 50 ch. The duration of the emission of the scattered light, however, ranges from 40 to 220 ch in the case of Streptococci (1) and from 30 to 170 ch in the case of Streptococci (2), and it shows expansion regardless of the intensity of the scattered light. In other words, this shows that the increased bacteria manifested a small diameter and a chain-link formation that increased in length.

Figure 27A:
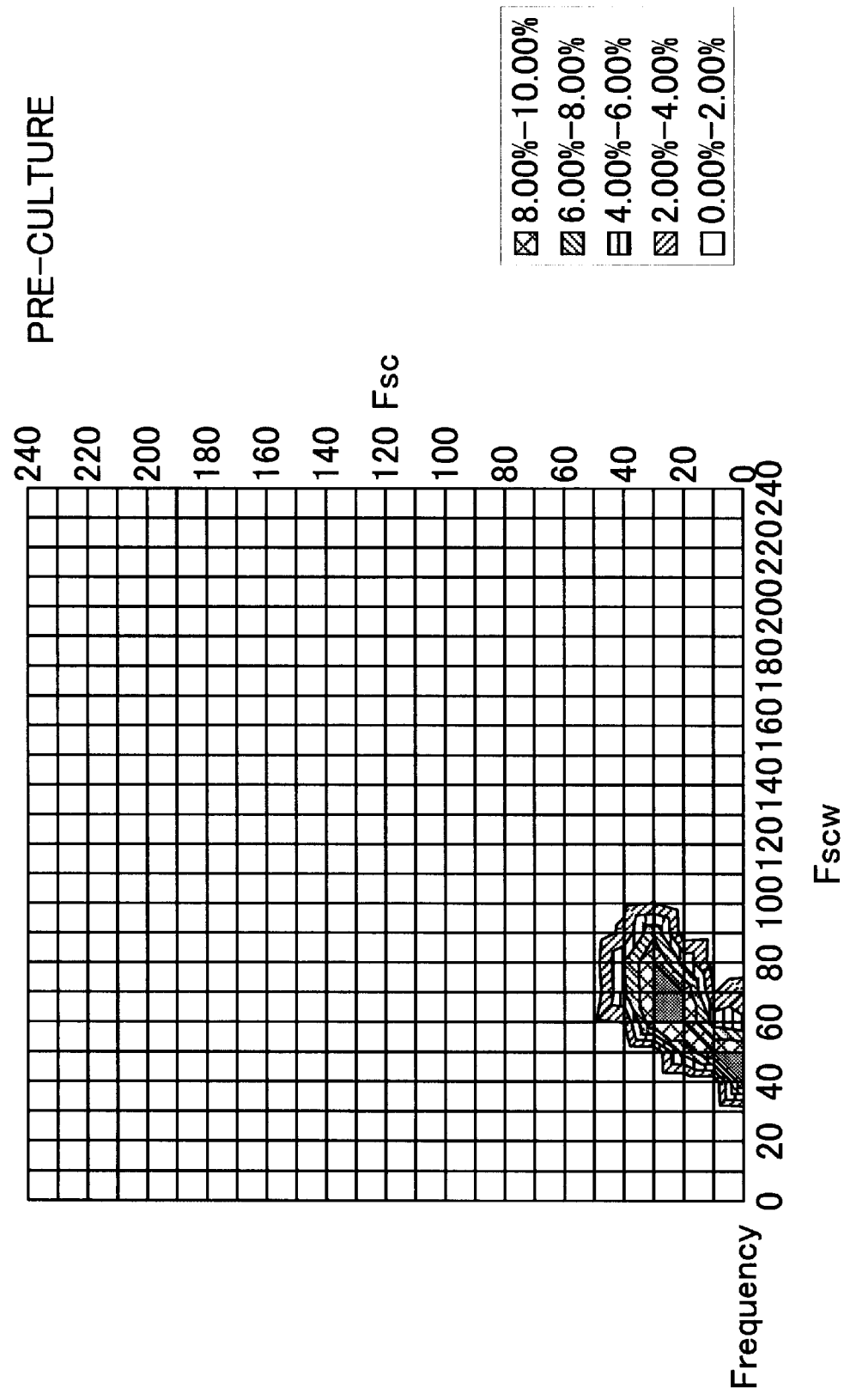
FIG. 27 graphs particle-size distribution assay results Streptobacilli (1)

FIG. 27 represents the analytical results for the Streptobacilli, which shows the bacteria prior to and following culture and changes in the particle-size distribution. Since the targeted culture is a concatenated Bacilli, the intensity of the scattered light in the increased bacteria ranges narrowly, primarily from 30 to 60 ch. The duration of the emission of the scattered light, however, ranges from 60 to 180 ch, and it shows expansion regardless of the intensity of the scattered light. In other words, this shows that bacteria with a small diameter increased in concatenated form. The Streptococci and the Streptobacilli both manifested an increase in the duration of the emission of the scattered light, pursuant to the degree of the chain-link formation of the bacteria. The intensity of the scattered light, however, is dependent on the diameter of each bacteria. Thus, since the diameter of the Streptobacilli is larger than that of the Streptococci, the intensity of the scattered light is also increasing.

Figure 28A:
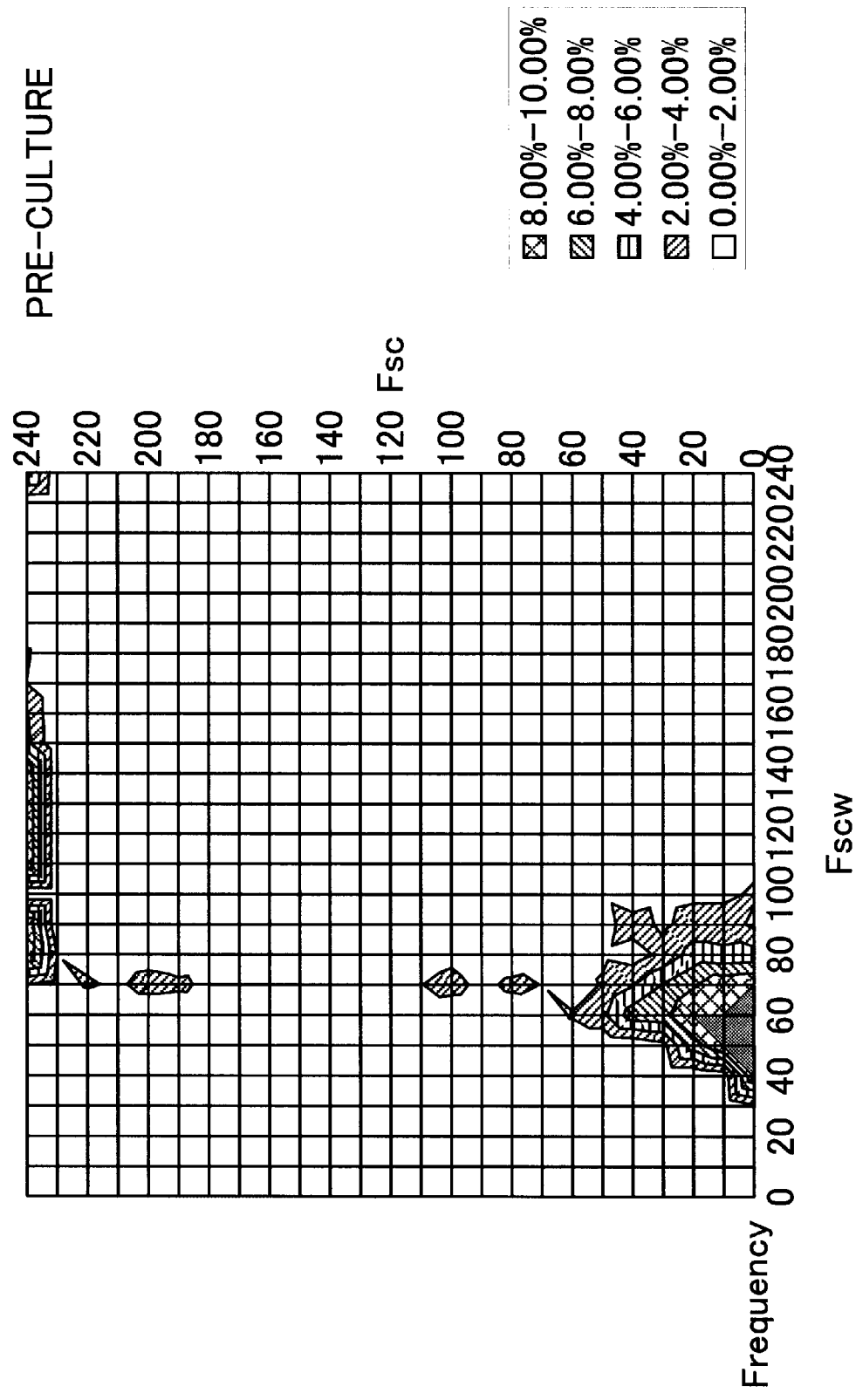
FIG. 28 graphs particle-size distribution assay results Streptobacilli (2)

FIG. 28 represents the analytical results for the yeast fungi, which shows the bacteria prior to and following culture and changes in the particle-size distribution. Since the targeted culture is a yeast fungi bacteria, the intensity of the scattered light in the increased bacteria is in the area of 240 ch on the figure, but this includes signals larger than 240 ch. Moreover, the duration of the emission of the light ranges from 60 to 150 ch.

It has been shown from this that, based on the analytical results of the increased cultured bacteria, a user can classify the increased bacteria into their appropriate categories: the Bacilli, the Staphylococci, the Streptococci, the Streptobacilli or the yeast fungi. Moreover, based on the analytical results and by means of the signal-processing unit 10, it is also possible to determine into which of the five categories the increased bacteria belong. For example, one can prescribe in advance the block section region of the particle-size distribution for each of the five classifications and show the classification results, in accordance with the number of signals in each of the block section regions. Furthermore, one can classify the bacteria by analyzing the peak position and the distribution width of the particle-size analysis.

In addition, it is well known that, when urine is used as the specimen, the Bacilli and the Streptobacilli bacteria in the urine are almost entirely Gram-negative and that the Staphylococci and the Streptococci in the urine are almost entirely Gram-positive. Accordingly, it is possible to infer the classification of the bacteria, based on the analytical results of said increased bacteria, and it is even possible to infer whether they will be Gram-positive or negative.

Various details of the present invention may be changed without departing from its spirit nor its scope. Furthermore, the foregoing description of the embodiments according to the present invention are provided for illustration only, and not for the purpose of limiting the invention as defined by the appended claims and their equivalents.

What is claimed is:

1. A method for measuring microorganisms within a culture sample wherein the specimen to be measured has been added to a culture solution, the method for measuring microorganisms comprising:

a first measurement process for obtaining a first particle-size distribution of said culture sample from optical information obtained from scattered light detected by using a flow cytometer to measure said culture sample after culture for a prescribed time;

a second measurement process for obtaining a second particle-size distribution of said culture sample from the optical information obtained from the scattered light detected by using said flow cytometer to measure said culture sample before culture;

an analysis process for obtaining a particle-size distribution of microorganisms cultured in said culture sample from the difference between said first particle-size distribution and said second particle-size distribution; and an output process for outputting said obtained microorganism particle-size distribution.

2. The method for measuring microorganisms recited in claim 1, wherein the emission duration and intensity of the scattered light signals detected by using said flow cytometer are measured to obtain said first and second particle-size distributions.

3. The method for measuring microorganisms recited in claim 1, wherein the emission duration and intensity of the scattered light signals detected by using said flow cytometer are measured to obtain the particle-size distribution of said cultured microorganisms, to infer the growth form of said microorganisms based on said particle-size distribution, and to determine to which prescribed category said microorganisms belong.

4. The method for measuring microorganisms recited in claim 1, wherein the emission duration and intensity of the scattered light signals detected by using said flow cytometer are measured to obtain the particle-size distribution of said cultured microorganisms, and the category to which each of said growth forms of said microorganisms belongs, from among the Staphylococcus, Streptococcus, Streptobacillus and the Bacillus varieties, is determined based on said particle-size distribution.

5. The method for measuring microorganisms recited in claim 1, wherein the specimen to be measured is urine.

6. The method for measuring microorganisms recited in claim 1, wherein the microorganisms that are measured are bacteria and/or yeast fungi.

7. A microorganism analyzer, used with a flow cytometer that measures the particle size of microorganisms in a culture sample wherein the specimen to be measured has been added to a culture solution, comprising:

a first measurement means for obtaining a first particle-size distribution of a culture sample after a prescribed period of culture, using optical information obtained from the scattered light detected by said flow cytometer;

a second measurement means for obtaining a second particle-size distribution of a culture sample before culture, using optical information obtained from the scattered light detected by said flow cytometer;

analysis means for obtaining a particle-size distribution of microorganisms cultured in said culture sample from the difference between said first particle-size distribution and said second particle-size distribution; and output means for outputting said obtained microorganism particle-size distribution.

8. In a computer-readable recording medium used with a flow cytometer that measures the particle size of microorganisms within a culture sample wherein the specimen to be measured has been added to a culture solution, said recording medium containing an analytical program to analyze the measurement results of said particle size, a computer-readable recording medium containing an analytical program that executes:

(A) a stage for obtaining a first particle-size distribution of a culture sample after a prescribed period of culture, using optical information obtained from the scattered light detected by said flow cytometer;

(B) a stage for obtaining a second particle-size distribution of the culture sample before said culture, using optical information obtained from the scattered light detected by said flow cytometer;

(C) a stage for obtaining a particle-size distribution of microorganisms cultured in said culture sample from the difference between said first particle-size distribution and said second particle-size distribution; and (D) a stage for outputting said obtained microorganism particle-size distribution.

* * * * *